United States Patent [19]
Williams et al.

[11] Patent Number: 5,955,354
[45] Date of Patent: Sep. 21, 1999

[54] RAS P21-INTERACTING PROTEIN (RGL) AND ITS RAS INTERACTING DOMAIN (RID)

[75] Inventors: Lewis T. Williams, Tiburon; Susan Demo, San Francisco, both of Calif.

[73] Assignee: The Regents of the University of California, Oakland, Calif.

[21] Appl. No.: 08/408,519

[22] Filed: Mar. 20, 1995

[51] Int. Cl.[6] ......................... C07H 21/04; C12N 15/63; C12N 15/79; A61K 38/17
[52] U.S. Cl. ............................. 435/320.1; 514/2; 514/12; 530/350; 536/23.5; 536/24.31
[58] Field of Search ................................ 435/69.1, 240.1, 435/325, 320.1; 514/2, 12; 530/350; 536/23.5, 24.31

[56] References Cited

PUBLICATIONS

Mayer et al., *Mol. & Cell. Bio*, vol. 12, pp. 609–618, 1992.
Demo et al., *Proc. Int. Symp. Princess Takamatsu Cancer Res. Fund*, 24th, pp. 243–249, 1994.
Albright et al., "Characterization of a guanine nucleotide dissociation stimulator for a–ras–related GTPase," *EMBO J.*, 12 (1):339–347 (1993).
Chevray et al. "Protein interaction cloning in yeadt: identification of mammalian proteins that react with the leucine zipper of Jun," *Proc. Natl. Acad. Sci. USA*, 89:5789–5793 (1992).
Fields et al., "A novel genetic system to detect protein–protein interactions," *Nature (London)*, 340:245–246 (1989).
Kikuchi et al., "ralGDS Family Members Interact with the Effector Loop as ras p21," *Molecular and Cellular Biology*, 14(11): 7483–7491 (1994).
Kikuchi et al., "The Post–translational Modification of ras p21 Is Important for Ras–1 Activation," *J. Biol. Chem.*, 269(31) :20054–20059 (1994).
Koide et al., "GTP–dependent association of Raf–1 with Ha–Ras: Identification of Raf as a target downstream of Ras in mammalian cells," *Proc. Natl. Acad. Sci. USA*, 90:8683–8686 (1993).
Lowry et al., "Function and Regulation of ras," *Annu. Rev. Biochem.*, 62:851–897 (1993).
Spaargaren et al., "Identification of the guanine nucleotide dissociation stimulator for Ral as a putative effector molecule of R–ras, H–ras, K–ras, and Rap" *Proc. Natl. Acad. Sci. USA*, 91:12609–12613 (1994).
Van Aelst et al., "Complex formation between RAS and RAF and other protein kinases," *Proc. Natl. Acad. Sci. USA*, 90:6213–6217 (1993).
Vojtek et al., "Mammalian Ras Interacts Directly with the Serine/Threonine Kinase Raf," *Cell*, 74:205–214 (1993).
Warne et al., Direct interaction of Ras and the amino–terminal region of Raf–1 in vitro, *Nature (London )*, 364:352–355 (1993).
Zhang et al., "Normal and oncogenic p21$^{ras}$ proteins bind to the amino–terminal regulatory domain of c–Raf–1," *Nature (London)*, 364:308–313 (1993).

*Primary Examiner*—Paula K. Hutzell
*Assistant Examiner*—Stephen Gucker
*Attorney, Agent, or Firm*—Townsend and Townsend and Crew, LLP

[57] ABSTRACT

A novel protein which interacts with ras p21, has been identified. This protein, RGL, shares 69% amino acid homology with ral guanine nucleotide dissociation stimulator (ralGDS). ralGDS was also found to bind ras p21. The ras p21-interacting domain of RGL (RID) bound to ras p21 through the effector loop of ras p21. Polypeptide and polynucleotide compositions of the RGL protein are provided as well as methods for implementing the diagnostic and therapeutic uses of these compositions. The uses include isolating effector proteins of ras p21 and modulating ras activity.

9 Claims, 10 Drawing Sheets

```
         10         20         30         40         50         60         70         80         90
AATTCGGCACGAGGCGTCGCGCGGGCGGGCGGGGCAGTCGGGCGCGCAAGGCGCGTGGGAAGCGCGGGGACCCGGAGCCGGGCCAG 100        110        120        130        140        150        160        170        180
AGAGACGCCCCGACCTCGGACAGGCGCGCACCATGCAGCGTCCGTGTGCCGGAAAGAAAACTGAGAATGAAATTACTTTGGCAAGCT
                                     M  K  L  L  W  Q  A 190        200        210        220        230        240        250        260        270
AAAATGAGCTCGATTCAGGACTGGGGTGAAGAGGTAGAGGAGGAGCTGTTTACCATGTCACCCCTCAAAAGAGTCCAGATTCAACAGGCG
 K  M  S  S  I  Q  D  W  G  E  E  V  E  E  E  G  A  V  Y  E  V  T  L  K  R  V  Q  I  Q  Q  A 280        290        300        310        320        330        340        350        360
GCCAATAAAGGAGGCGAGATGGCTAGGTGGCTGGGTGAAGGGGACCAGCTGCCTCCAGGACACAGTCAGTACGAGACCTGCAAGATCAGG
 A  N  K  G  A  R  W  L  G  V  E  G  D  Q  L  P  P  G  H  T  V  S  Q  Y  E  T  C  K  I  R 370        380        390        400        410        420        430        440        450
ACCATCAAAGCTGGTACGCTGGAGAAGCTTGTGGAGAACCTGCTGACGGCTTTTGGGGACAATGACTTTACCTACATCAGCATCTTTTTG
 T  I  K  A  G  T  L  E  K  L  V  E  N  L  L  T  A  F  G  D  N  D  F  T  Y  I  S  I  F  L 460        470        480        490        500        510        520        530        540
TCGACATACAGAGGCTTTGCCTCGACTAAGGAAGTGCTGGAGCTGCTGGATCGGTATGGAAACCTGACAGGCCCCAACTGTGAAGAC
 S  T  Y  R  G  F  A  S  T  K  E  V  L  E  L  L  D  R  Y  G  N  L  T  G  P  N  C  E  D 550        560        570        580        590        600        610        620        630
GATGGAAGCCAAAGTTCACCCGAGTCCAAGGCCGTGATCCGGAATGCCATTGCTTCCATCCTGAGGGCCTGGCTTGACCAGTGTGCGGAA
 D  G  S  Q  S  S  P  E  S  K  A  V  I  R  N  A  I  A  S  I  L  R  A  W  L  D  Q  C  A  E
```

*FIG. 1A-1.*

```
     640         650         660         670         680         690         700         710         720
GACTTCCGGGAGCCCCCTCACTTCCCTTGCCTTCAGAAGCTGCTGGAGTACCTCAAACAGATGATGCCTGGCTCTGACCCAGAGAGGAGA
 D   F   R   E   P   P   H   F   P   C   L   Q   K   L   L   E   Y   L   K   Q   M   M   P   G   S   D   P   E   R   R 730         740         750         760         770         780         790         800         810
GCACAGAACCTTCTTGAACAGTTTCAAAAGCAGGACGTGGATTCCGACAATGGACTTCTCAACACCAGCTTCTCAGCTCTGGAAGAGGAA
 A   Q   N   L   E   Q   F   Q   K   Q   D   V   D   S   D   N   G   L   L   N   T   S   F   S   L   E   E   E 820         830         840         850         860         870         880         890         900
GAGGAACTGGAGAGCGGAGGGTCAGCAGAATTCACGAACTTCTCAGAGATCTCGTGGCAGAACAGTCTGACCTACATGGACGCACAACTA
 E   E   L   E   S   G   G   S   A   E   F   T   N   F   S   E   D   L   V   A   E   Q   L   T   Y   M   D   A   Q   L 910         920         930         940         950         960         970         980         990
TTCAAGAAGTAGTGCCTCACCATTGCCTGGGCTGTATTTGGTCTCAGCGGGATAAAAGGAAAAACAAGCATTTGGCTCCTACGATCCGT
 F   K   K   V   V   P   H   H   C   L   G   C   I   W   S   Q   R   D   K   K   E   N   K   H   L   A   P   T   I   R 1000        1010        1020        1030        1040        1050        1060        1070        1080
GCCACCATCTCAGTTTAATACGCTCACCAAGTGTGTTCAGCAGTCCGTCTGGGGAGCAAGGAACTCAAAACTCAGCAGCGAGCCAGA
 A   T   I   S   Q   F   N   T   L   T   K   C   V   V   S   T   V   L   G   S   K   E   L   K   T   Q   Q   R   A   R 1090        1100        1110        1120        1130        1140        1150        1160        1170
GTCATCGAGAAGTGGATCAACATTGCTCACGAATGCTAGAGATCCTGAAGAATTTTTCCTCCTTGAGGGCCATCGTTTCCGCACTGCAGTCT
 V   I   E   K   W   I   N   I   A   H   E   C   R   I   L   K   N   F   S   S   L   R   A   I   V   S   A   L   Q   S 1180        1190        1200        1210        1220        1230        1240        1250        1260
AATTCCATCTATCGGTTGAAAAAGGCTTGGGCTGCTGCCGAAGGACAGAATGCTGATGTTTGAAGAACTTTCAGATATCTTCTCTGAT
 N   S   I   Y   R   L   K   K   A   W   A   A   V   P   K   D   R   M   L   M   F   E   E   L   S   D   I   F   S   D
```

FIG. 1A-2.

```
      1270        1280        1290        1300        1310        1320        1330        1340        1350
CACAATAACCATCTAACCAGTCGGGAGCTACTAATGAAGGAAGAACTTCAAAATTTGCAAACCTGGACAGCAGGCGTGAAAGAAAACCAG
 H  N  N  H  L  T  S  R  E  L  L  M  K  E  E  L  Q  N  L  Q  T  W  T  A  G  V  K  E  N  Q 1360        1370        1380        1390        1400        1410        1420        1430        1440
AAGCGGACCCAGAGGCGCCTGCAACTGCAGAAGGATATGGGTGTGATGCAGGGTACCGTGCCTTACCTGGGCACCTTCCTGACTGACCTG
 K  R  T  Q  R  R  L  Q  L  Q  K  D  M  G  V  M  Q  G  T  V  P  Y  L  G  T  F  L  T  D  L 1450        1460        1470        1480        1490        1500        1510        1520        1530
ACCATGCTGGACACTGCCCTGCAGGACTACATTGAGGGTGGACTGATCAACTTCGAGAAAAGAAGAGAATTTGAAGTCATTGCCCAG
 T  M  L  D  T  A  L  Q  D  Y  I  E  G  G  L  I  N  F  E  K  R  R  E  F  E  V  I  A  Q 1540        1550        1560        1570        1580        1590        1600        1610        1620
ATAAAGCTCCTACAGTCTGCTTGCAACAGCTACTGCATGGGCCCAGATCAGAAGTTTATCCAGTGGTTCCAGAGGCAGCAGCTTCTATCA
 I  K  L  L  Q  S  A  C  N  S  Y  C  M  G  P  D  Q  K  F  I  Q  W  F  Q  R  Q  Q  L  L  S 1630        1640        1650        1660        1670        1680        1690        1700        1710
GAGGAGAAAGTACGCCCCTCTCGTGAGATTGAAGCCGCTGCCGACGCCAACACCACTTCCCCTAAGCCTCGGAAAGCATGGTGAAG
 E  E  S  Y  A  L  S  C  E  I  E  A  A  A  D  A  N  T  T  S  P  K  P  R  K  S  M  V  K 1720        1730        1740        1750        1760        1770        1780        1790        1800
AGGCTGAGCCTGCTATTTCTGGGGTCTGACATCATCCCCGGGAGCACTCCCACCAAAGAGCAGCCCAAGTCCGCAGCCAGTGGGAGCTCT
 R  L  S  L  L  F  L  G  S  D  I  I  P  G  S  T  P  T  K  E  Q  P  K  S  A  A  S  G  S  S 1810        1820        1830        1840        1850        1860        1870        1880        1890
GGGGAGAGTATGGACTCAGTCAGTGTGTCCTGTGAATCAAACCACTCCGAGGCTGAGGAGGGCCCCGTCACACCCATGGACACACCA
 G  E  S  M  D  S  V  S  V  S  S  C  E  S  N  H  S  E  A  E  E  G  P  V  T  P  M  D  T  P
```

FIG. 1A-3.

```
     1900        1910        1920        1930        1940        1950        1960        1970        1980
GATGAGCCCCAAAGAAGCTCTCTGAATCCTCCTCTTCCTGTTCCTCCATCCATTCCATGGACACGAATTCCTCAGGGATGTCGTCCCTA
  D  E  P  Q  K  K  L  S  E  S  S  S  S  C  S  S  I  H  S  M  D  T  N  S  S  G  M  S  S  L 1990        2000        2010        2020        2030        2040        2050        2060        2070
ATCAACCCCCTGTCCTCCCCTCAAGTGCAACAACAATCCTAAAATCCACAAGCGCTCCGTCTCCGTGACATCCATTACCTCCACAGTA
  I  N  P  L  S  S  P  P  T  C  N  N  N  P  K  I  H  K  R  S  V  S  V  T  S  I  T  S  T  V 2080        2090        2100        2110        2120        2130        2140        2150        2160
CTGCCTCCTGTTTACAATCAGCAGAATGAAGAACACCTGCATCATCCGCATCAGTGTAGAAGACAACAATGGCCACATGTACAAGAGCATC
  L  P  P  V  Y  N  Q  Q  N  E  D  T  C  I  I  R  I  S  V  E  D  N  N  G  H  M  Y  K  S  I 2170        2180        2190        2200        2210        2220        2230        2240        2250
ATGCTGACAAGCCAGGATAAGACCCCCGCTGTGATCCAGAGAGCGATGTCGAAGCACAACCTGGAGTCGGACCCCGCCGAGGAGTATGAG
  M  L  T  S  Q  D  K  T  P  A  V  I  Q  R  A  M  S  K  H  N  L  E  S  D  P  A  E  E  Y  E 2260        2270        2280        2290        2300        2310        2320        2330        2340
CTGGTGCAGGTCATCTCGGAGGACAAAGAACTAGTGATCCCGGACTCTGCAAACGTCTTTTACGCCATGAATAGCCAAGTGAACTTTGAT
  L  V  Q  V  I  S  E  D  K  E  L  V  I  P  D  S  A  N  V  F  Y  A  M  N  S  Q  V  N  F  D 2350        2360        2370        2380        2390        2400        2410        2420        2430
TTCATTTTACGCAAAAAGAACTCGGTGGAGGAGCAGGTGAAGTTGCGCAGCCGTCGGACCTGACTTTGCCCAGGACAGCTAAGCGGGGC
  F  I  L  R  K  K  N  S  V  E  E  Q  V  K  L  R  S  R  T  S  L  T  L  P  R  T  A  K  R  G 2440        2450        2460        2470        2480        2490        2500        2510        2520
TGCTGGAGTAACAGGCACAGCAAGATCACCCTCTGAAAGGGACAGTACACTCCTACTGCCCAAGGCAGAGTGAGGCTGAGCAAAAGCCAT
  C  W  S  N  R  H  S  K  I  T  L  *
```

*FIG. 1A-4.*

```
       2530        2540        2550        2560        2570        2580        2590        2600        2610
GGCGACGCCAACCACCCAGTGTTGAGCATCATTGGTGAAAGCGACAGATATTTATAGAATTCAGCTGTGCAGAGAGCACTGTGCAGG
       2620        2630        2640        2650        2660        2670
GGAGAGTGGAAGTGAATTTGACATTAAAAGGATAAAAGGTTCAAAAAAAAAAAAAAAAA
```

```
RGL      1 MKLLWQAKMGSITDWGEDVEEGAVYHVTTKRVQIQTAANKGARWLGVEGDQLP    53
ralGDS   1 MMVDCQGSTTEIGEDLINGVITSISTRKVQLHTGATKGQRWLGCENES..      48

RGL     54 PGHTVSQYETCKIRTIKAGTLEKLVENILTAEGDNDFTYISIFLSTYRGF      103
ralGDS  49 ...ALNLYETCKVRTVKAGTLEKLVEHIVPAFQGSDLSYVTVFLCTYRAF       95

RGL    104 ASIKEVIELILDRYG...NLTGP...NYEDDGSQSSPESKAVIRNAIASI      147
ralGDS  96 TTIQQVIDLIFKRYGRCDALTASSRYGYILPYSSEDGGPQDQLKNAISSI      145

RGL    148 LRAWLDQCAEDFREPPHFPCDQKILEYLKQMNFGSDPERRAQNLIEIFQ.      196
ralGDS 146 LGTWLDQYSEDFCQPPDFPCDKQIVAYVQLNNFGSDLERRAHLLIAILED      195

RGL    197 ..........................KQDVDSDNGLINI..........      209
ralGDS 196 LEPSEAESEALSPAPVLSLKPASQLEPALILIPSQVVTSTPVREPAAAPV      245

RGL    246 ..................................................      295
ralGDS 246 PVLASSPVVAPAPELEPVPEPPQEPEPSLALAPELEPAVSQSLELESAPV      295

RGL    210 ......SSFSLEEEELESGGSAEFTNFSEDLVAEQLTYMDAQLFKKVVP       253
ralGDS 296 PTPALEPSWSLPEATENGLTEKPHLLLFPPDLVAEQFTLMDAELFKKVVP       345

RGL    254 HHCLGCIWSQRDKKENKELAPTIRATISDFNTLTKCVVSTVLGSKELKTQ      303
ralGDS 346 YHCLGSIWSQRAKKGKELAPTIRATIRATVADFNNVANCVITTCLGDQSMKAP   395

RGL    304 QRARVIEKWINIAHECRILKNFSSLRAIVSALQSNSIYRLKKAKAAVPKD      353
ralGDS 396 DRARVVEHWIEVARECRALKNFSSLYAILSALQSNAIHRLKKTKEEVSRD      445
```

FIG. 1B-1.

```
RGL    354 RMLMFEELSDIFSDHNNHLTSRELLMKEGTSKFANDDSSVKENQKRTQRR       403
ralGDS 446 SFRVFQKLSEIFSDENNYSLSRELLIKEGTSKFATDE....MNPRRAQRR       491

RGL    404 LQLQKDMGVMQGTVPYLGTFLTDLTMLDTALQDYIEGGLINFEKRFREEE       453
ralGDS 492 ...QKETGVIQGTVPYLGTFLTDLVMLDTAMKDYLYGRLINFEKRFKEEE       538

RGL    454 VIAQIKLLQSACNSYCMGPDQKFIQWFQRQQLLSFEESYALSCEIEAAAD       503
ralGDS 539 VIAQIKLLQSACNNYSIAPEEHFGTWFRAMERLSFAESYTLSCELEPPSE       588

RGL    504 ..ANTTSPKPRKSMVKFLSLLFLGSDIIPGSTPTK....ECPKSAASGSS       547
ralGDS 589 SASNTLRSKKSTAIVKFWSDRQAPSTELSTSSSAHSKSCDCLRCSPYLGS       638

RGL    548 GESMDSVSVSSCESNHSEAEEGPVT.PMDTPDEPQKKLSESSSSCSSIHS       596
ralGDS 639 GDITDALSVHSAGSSSSDVEEINMSFVPESPDGQEKKFWESASQSSPETS       688

RGL    597 MDINSSGMSSLINPLSSPPICNNNPKIHKRSVSVTSITSTVLPPVYNQQN       646
ralGDS 689 GIISASSSTS...SSSASTIPVSTTRTHKRSVSVGVCSYSSSL.PLYNQQV       734

RGL    647 EDTCIIRISVEDNNGHMYKSIMLTSQDKTPAVIQRAMSKHNLESDPAEEY       696
ralGDS 735 GDCCIIRVSLDVDNGNMYKSILVTSQDKAPTVIRKAMDKHNLDEDEPEDY       784

RGL    697 ELVQVISEDKELVIPDSANVFYAMNSQVNFDFILRKKNSVEEQVKLRSRT       746
ralGDS 785 ELVQIISEDHKLKIPENANVFYAMNSTANYDFIL.KKRTFTKGAKVKHGA       833

RGL    747 SLTLPRTAKRGCWSNRHSKITL                                    768
ralGDS 834 SSTLPRMKQKGLRIAKGIF                                       852
```

RAS P21-INTERACTING PROTEIN (RGL) AND ITS RAS INTERACTING DOMAIN (RID)

This invention was made with government support under Grant No. HL07731, awarded by the National Institutes of Health. The government has certain rights in this invention.

BACKGROUND OF THE INVENTION ras p21 is a member of the small GTP-binding protein (G-protein) superfamily. ras proteins are thought to regulate key signalling pathways involved in cell growth and development. ras proteins reside on the inner surface of the plasma membrane where they participate in transmitting signals from tyrosine kinase receptors and some receptors coupled to heterotrimeric G proteins.

Because mutated ras proteins have been found in lung, bladder, colon, and many other human carcinomas, and are associated with human carcinogenesis, it is of value to study the processes by which ras mediates cell proliferation and differentiation. One approach to dissecting ras function is to identify and study the molecules that interact with ras, specifically the regulatory and effector molecules of ras p21. Knowledge of the interacting proteins in the ras signaling pathway will allow the screening of drugs for agonists and antagonists of ras-dependent cell proliferation and differentiation. Until recently, the hunt for direct downstream targets through which ras acts has not been fruitful. The discoveries of the present invention provide tools useful to elucidate the mechanism of ras signaling and new approaches to modulate ras activity and to alleviate disease conditions due to ras dysfunction.

SUMMARY OF THE INVENTION ras p21 is a member of the small GTP-binding protein (G-protein) superfamily. ras proteins regulate key signalling pathways involved in cell growth and development. A novel protein, RGL, which interacts with ras p21, has been identified. RGL was found to share 69% amino acid homology with ral guanine nucleotide dissociation stimulator (ralGDS), a GDP/GTP exchange protein for ral p24, ralGDS was similarly tested and was found to bind ras p21. It was found that the ras p21-interacting domain of RGL (RID) binds to ras p21 through the effector loop of ras p21.

The present invention provides the nucleotide and amino acid sequence of RGL as well as polypeptide and polynucleotide compositions based on RGL, including the RID of RGL. The uses and methods of use of the RGL polynucleotide and polypeptide compositions are disclosed.

One aspect of this invention is to provide an isolated polynucleotide comprising at least 80% sequence identity with the nucleotide sequence of SEQ ID NO:1, an allelic or species variation thereof, or a fragment thereof. A polynucleotide comprising the nucleotide sequence of SEQ ID NO:1 or the sequence of SEQ ID NO:3 is provided.

Another aspect of the invention is to provide an isolated polypeptide comprising the sequence of SEQ ID NO:2, an allelic or species variation thereof, or a fragment thereof. An isolated polypeptide comprising the sequence of SEQ ID NO:4, or at least 80% sequence identity to SEQ ID NO:4, is also provided. In a specific embodiment, the polypeptide is one capable of binding the effector loop of ras p21.

Another aspect of the invention is to provide an isolated polypeptide comprising the sequence of SEQ ID NO:2, an allelic or species variation thereof, or a fragment thereof, wherein the isolated polypeptide is a fusion protein. A RID-GAL4 fusion protein is specifically provided. In one aspect, the fusion protein comprises a tag, or a product of a second gene or fragment of that second gene product. A polypeptide is provided wherein the tag is GST, an epitope tag or an enzyme or wherein the second gene is lacZ.

A further aspect of the invention is to provide a recombinant DNA molecule comprising the nucleotide sequence of SEQ ID NO:1 or a fragment thereof. In one embodiment, the recombinant DNA molecule is pGAD/RID encoding a RID-GAL4 transactivation domain fusion protein. A recombination DNA molecule, pGAD/ralGDS, encoding a ralGDS-GAL4 transactivation domain fusion protein is also provided. A cell is provide which contains the recombinant DNA molecule comprising the nucleotide sequence of SEQ ID NO:1 or a fragment thereof.

Yet another aspect of the invention is the provision of antibodies that specifically bind a polypeptide comprising the sequence of SEQ ID NO:2, an allelic or species variation thereof, or a fragment thereof. In one embodiment, an antibody specifically binds to the polypeptide comprising the sequence of SEQ ID NO:4. These antibodies can be polyclonal or monoclonal. A hybridoma capable of producing a monoclonal antibody to any one of these described polypeptides is provided. Also provided is a kit comprising any antibody preparation to the above-mentioned polypeptides.

In a different aspect of the invention, a method is provided for isolating a RGL gene or fragment thereof, comprising screening a DNA library using a RGL probe to identify a hybridizing clone and isolating said RGL gene or gene fragment from said hybridizing clone. An RGL probe suitable for use in this method is one which comprises the nucleotide sequence of SEQ ID NO:1 or a fragment thereof. The method is useful to isolate a human RGL gene as well as RGL genes from other species.

A further aspect of the invention is to provide a method of identifying a gene encoding a ras p21-binding protein. The method comprises screening a DNA library with a RID probe to identify a hybridizing clone containing a RID sequence, the presence of a RID sequence being indicative of a gene encoding a ras p21-binding protein. Provided for use in this method is a RID probe comprising the sequence of SEQ ID NO:3 or a fragment thereof. The method is useful to identify genes encoding ras p21-binding proteins which are regulators or an effector proteins of ras p21.

The invention also provides a method of identifying a ras effector loop-binding protein, comprising screening a gene library with an RID probe for a gene that is substantially homologous to the RGL gene, isolating the substantially homologous gene, producing a polypeptide encoded by the substantially homologous gene and finally determining if the polypeptide binds an effector loop of a ras protein, binding indicating that the polypeptide is a ras effector loop-binding protein.

Another aspect of the invention is to provide a method of modulating or blocking ras p21 activity comprising providing a RID polypeptide in a cell expressing ras p21 protein wherein said RID polypeptide binds to said ras p21 protein to block ras p21 activity. In one embodiment, the RID polypeptide is provided by introducing an expression vector encoding a RID polypeptide into the ras p21 expressing cell. The RID polypeptide for use in this method will be derived from the RGL or ralGDS proteins.

It is yet another aspect of the invention to provide a method of blocking a ras p21 protein binding to a ras effector protein in a cell whereby the method comprises expressing a RID polypeptide from a RGL or a ralGDS protein in a cell. The ras effector protein can be Raf, GAP, NF1 or PI (3)K.

Another aspect of the invention is a method of isolating a RGL interacting protein, comprising contacting a cell lysate suspected of containing a RGL interacting protein with a RGL polypeptide and isolating any protein bound to the RGL polypeptide, as a RGL interacting protein. If the RGL interacting protein is ras p21, a RID polypeptide can be used to bind and isolate ras.

The invention further provides a pharmaceutical composition useful in the treatment of a cell proliferative condition, the composition comprising a RID polypeptide and a pharmaceutically acceptable carrier. A second pharmaceutical composition useful for the same purpose includes an expression vector capable of expressing a RID polypeptide in an affected cell and a pharmaceutically acceptable carrier.

It is another aspect of the invention to provide a method of alleviating a patient suffering from a cell proliferative condition, comprising administering to the patient, a therapeutically effective amount of the pharmaceutical composition described above. This method is useful to treat such cell proliferative conditions as cancer or restenosis caused by ras dysfunction.

BRIEF DESCRIPTION OF THE DRAWINGS

FIG. 1B shows alignment of the amino acid sequences of RGL (SEQ ID NO:2) and ralGDS (SEQ ID NO:5). Sequences were aligned by using the Best Fit program. Amino acid identity is denoted by a black background. Dots indicate gaps. ralGDS refers to mouse ralGDSa.

FIG. 4A shows the time course for the GAP inhibition activity of ralGDS. The [γ-$^{32}$P]GTP-bound form of ras p21 was incubated for the indicated periods of time with or without 300 nM ralGDS in the presence or absence of 10 nM GST-NF1. The mixtures were then collected on filters, washed, and counted. Δ, without ralGDS or GST-NF1; ▲, with ralGDS; □, with GST-NF1, ●, with ralGDS and GST-NF1.

FIG. 4B shows the dose-dependent effect of ralGDS and Raf on GAP inhibition activity. The [γ-$^{32}$ P]GTP-bound form of ras p21 was incubated for 6 min with the indicated amounts of ralGDS or GST-N-Raf. ●, with ralGDS; ○, with GST-N-Raf.

Figures 1, 1A, 1C, 2, 3, 4, 5:
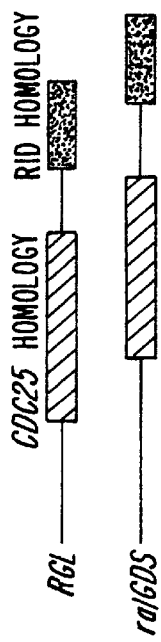
FIG. 1A shows the nucleotide (SEQ ID NO: 1) and predicted amino acid sequences (SEQ ID NO: 2) of a 2.7 kb cDNA encoding RGL. The single-letter amino acid code is shown below the DNA sequence.
FIG. 1C is a schematic representation of RGL and ralGDS sequence homology.
FIG. 5 shows the inhibition of the interaction of Raf-1 with ras p21 by ralGDS. The [α-$^{32}$P]GTP-bound form of ras p21 was incubated for 30 min with 20 nM GST-N-Raf in the presence of the indicated amounts of ralGDS. GST-N-Raf was precipitated by using glutathione-Sepharose 4B, the precipitates were washed, and the remaining radioactivity was counted.

DESCRIPTION OF THE PREFERRED EMBODIMENT ras p21 is a member of the small GTP-binding protein (G-protein) superfamily and plays an important role in cell growth and differentiation.

Mammalian ras genes are expressed in all cell lineages and organs. ras is synthesized in the cytosol and mature ras becomes associated with the inner side of the plasma membrane after posttranslational modifications where it participates in transmitting signals from tyrosine kinase receptors and some receptors coupled to heterotrimeric G proteins.

ras p21 has GDP/GTP-binding and GTPase activities and cycles between the GDP-bound inactive and GTP-bound active forms. The GDP-bound inactive form can be activated by guanine nucleotide exchange proteins (Lowy et al., Annu. Rev. Biochem., 62:851–891 (1993)) which promote the exchange of GDP for GTP, thereby converting ras p21 to the GTP-bound active form. ras proteins are then deactivated by interaction with GTPase-activating proteins (GAPs) that promote GTP hydrolysis by ras. Without being bound by a particular theory, it is presumed that the GTP-bound active form of ras p21 interacts with effector proteins that can mediate ras p21-dependent processes such as growth factor-stimulated cell proliferation.

Identification of effector proteins of the active form of ras has been difficult. One candidate effector protein of ras p21 is Raf, a cytoplasmic serine/threonine protein kinase that has been previously shown to act downstream of ras p21 (Dickson et al., Nature (London), 360:600–603 (1992) and Han et al., Nature (London), 363:133–140 (1993)). It has been recently demonstrated that Raf interacts with the GTP-bound but not with the GDP-bound form of ras p21, that Raf binds to the effector loop of ras p21 (Van Aelst et al., *Proc. Natl. Acad. Sci. USA*, 90:6213–6217 (1993); Vojtek et al., *Cell*, 74:205–214 (1993); and Warne et al., *Nature* (London), 364:352–355 (1993)), and that Raf inhibits the GTPase-activating activity of GTPase-activating protein (GAP), which is known to interact with the effector loop of ras p21 (Warne, supra and Zhang et al., *Nature* (London), 364:308–313 (1993)). These results have indicated that Raf is an effector protein of ras p21, consistent with previous observations that Raf acts downstream of ras p21 in signaling pathways that mediate both the differentiation and mitogenic responses to receptor tyrosine kinases (Dickson et al., supra and Han et al., supra). However, it is possible that ras p21 has effector proteins other than Raf, since ras p21 has multiple functions (Lowy, supra).

The present invention identifies a novel protein that interacts with ras p21 in the yeast two-hybrid system. This protein, termed RGL (ralGDS-like), is highly homologous with ral guanine nucleotide dissociation stimulation (ralGDS), a GDP/GTP exchange protein for ral p24, a member of small G-protein superfamily and a 115-kD protein (Albright et al., *EMBO J.*, 12:339–347 (1993)). According to the present invention, the ras p21-binding domain of RGL binds to ras p21 through the effector loop of ras p21 and that this domain is highly conserved in ralGDS. Therefore, RGL and ralGDS were examined as to whether they could be effector proteins of ras p21. Since ralGDS has been well characterized, it was tested in this invention. Three characteristics that could be considered to be criteria for identification of an effector protein of ras p21 were tested: (i) the protein must interact with the GTP-bound active form of ras p21 but not with the GDP-bound inactive form, (ii) it must interact with ras p21 through the effector loop of ras p21, and (iii) ideally the protein should inhibit the interaction of ras p21 with other effector proteins such as Raf. By both in vitro and in vivo studies, it was demonstrated that ralGDS fulfills these three characteristics.

The yeast two-hybrid system (Chien et al., *PNAS*, 88:9578–9582 (1991)) allows detection of proteins capable of interacting with a known protein that results in the immediate availability of the cloned genes for these interacting proteins. Briefly, the method is as follows. Plasmids are constructed to encode two hybrid proteins which are coexpressed in *Saccharomyces cerevisiae*. One hybrid consists of the DNA-binding domain of the yeast transcriptional activator protein GAL4 fused to the known protein; the other hybrid consists of the GAL4 activation domain fused to protein sequences encoded by a library of yeast genomic DNA fragments. Interaction between the known protein and a protein encoded by one of the library plasmids lead to transcriptional activation of a reporter gene containing a binding site for GAL4. A suitable reporter gene is the *Saccharomyces cerevisiae* HIS3 gene and the *E. coli* lacZ gene (encoding β-galactosidase (β-gal)). Yeast cells are tested for growth in media lacking histidine and for expression of β-gal activity which can be assayed by detecting blue colonies on a plate containing the substrate 5-bromo-4-chloro-3-indolyl β-D-galactoside.

In the present invention, the yeast reporter strain is cotransformed with PC62/ras p21 which encodes a GAL4 DNA binding domain fused to c-H-ras, and P51/mouse embryonic cDNA library linked to the GAL4 transactivation domain.

A clone was identified that encodes a 164-amino-acid domain (RID) which interacts with H-ras p21. However, RID has no primary sequence homology with Raf and GAP, which interact with ras p21. Using this RID clone as a probe, cDNA of RGL was isolated and sequenced. The nucleotide and amino acid sequence of RGL is shown in FIG. 1A. The GenBank™ Accession number for the RGL sequence is U14103. It was found that RGL shares 69% amino acid homology with ralGDS. It was also found that the RIDs of RGL and ralGDS are located on the C-terminal side of the CDC25-like domains of these molecules. The high degree of homology between the RIDs of RGL and ralGDS indicates that these domains are functionally important. The findings of the present invention indicate that ralGDS and RGL are in a family of proteins that contain a domain that binds to ras p21.

Definitions

An "RGL interacting protein" or associated protein is one which has an affinity for RGL and binds or physically interacts with RGL. The term "RGL interacting molecule" does not imply any particular molecular size or other structural or compositional feature other than that the molecule or compound in question is capable of binding or otherwise interacting with RGL. This interaction can be transient, lasting only a fraction of a second or it can be stable so as to enable the detection of the complex of RGL-interacting molecule. Preferably, this interaction persists for at least ten seconds, ideally several minutes. The interacting molecule may be a substrate of RGL, an enzyme that acts on RGL, a protein that RGL is involved in localizing, an effector molecule of ras p21 or a molecule that alters the conformation of RGL upon interaction. Interacting or associating proteins that can be investigated by this invention include but are not restricted to agonists and antagonists for ras proteins, cellular proteins encoded by oncogenes or proto-oncogenes, lipids, toxins, hormones, sugars, cofactors, peptides, proteins, enzyme substrates, drugs and compounds from plant or animal sources.

The "effector loop of ras" is a region in ras defined by amino acids 30–38 known to bind to effector proteins of ras such as Raf, GAP or NF1.

A "ras effector protein" is a protein capable of transmitting signals from ras to various intracellular signalling cascades. Ras effector proteins include phosphatidylinositol-3-OH kinase (PI(3)K) and the kinases Raf, Mek and Erk. However, the identification of ras effector proteins as described in the present invention encompasses only those effector proteins that directly physically interact or associate with ras p21.

Unless stated otherwise, "RGL protein or polypeptide" as used herein refers to the full length RGL protein, the RID polypeptide, fusion proteins of both and mutant derivatives of these proteins or polypeptides. The full-length RGL polypeptide and naturally occurring mutants can be the isolated, naturally produced form or recombinantly synthesized. Preferably, all other derivatives will be produced recombinantly.

"RID" which stands for ras p21-interacting domain, is the carboxy-terminal 164 amino acid domain constituting amino acids 605–768 of the RGL protein. As the name suggests, RID interacts with ras p21, at the effector loop of ras. When the RID of ralGDS is mentioned, it refers to the region in the ralGDS protein that shares homology with the RID of RGL, the region encompassing amino acids 698–852 in ralGDS.

"CDC25-like domain" describes the region of RGL (amino acids 210 to 499) which is similar to a comparable region of CDC25, a GDP/GTP exchange protein for ras p21.

An "isolated polynucleotide" is a polynucleotide, e.g., an RNA, DNA, or a mixed polymer, which is substantially separated from other DNA sequences which naturally accompany a native human sequence, e.g., ribosomes, polymerases, and many other human genome sequences. The term embraces a polynucleotide sequence which has been removed from its naturally occurring environment, and includes recombinant or cloned DNA isolates and chemically synthesized analogues or analogues biologically synthesized by heterologous systems. A substantially pure molecule includes isolated forms of the molecule. An "isolated polypeptide" or protein carries a similar meaning with the polypeptide or protein being substantially separated from any cellular contaminants and components naturally associated with the protein in vivo.

An "allelic variation" in the context of a polynucleotide or a gene is an alternative form (allele) of a gene that exists in more than one form in the population. At the polypeptide level, "allelic variants" generally differ from one another by only one, or at most, a few amino acid substitutions. A "species variation" of a polynucleotide or a polypeptide is one in which the variation is naturally occurring among different species of an organism.

A "fragment" of a polynucleotide is a stretch of at least about 18 nucleotides, more typically at least about 40 nucleotides. A polypeptide "fragment" or "segment" is a stretch of amino acid residues of at least about 6 contiguous amino acids from a particular sequence, more typically at least about 12 amino acids.

The term "recombinant" or "recombinant DNA molecule" refers to a nucleic acid sequence which is not naturally occurring, or is made by the artificial combination of two otherwise separated segments of sequence. By "recombinantly produced" is meant artificial combination often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features may be incorporated by design. "Recombinant DNA molecules" include cloning and expression vectors.

Two nucleic acids or polynucleotides share sequence "homology" or "identity" if the two polynucleotides or designated segments thereof, when optimally aligned with appropriate nucleotide insertions or deletions, are identical in at least about 50% of the nucleotides. "Substantial homology" in the nucleic acid context means either that the segments, or their complementary strands, when compared, are identical when optimally aligned, with appropriate nucleotide insertions or deletions, in at least about 60% of the nucleotides, usually at least about 70%, more usually at least about 80%, preferably at least about 90%, and more preferably at least about 95 to 98% of the nucleotides. Alternatively, substantial homology exists when the segments will hybridize under selective hybridization conditions, to a strand, or its complement, typically using a sequence derived from the RID or other regions of the RGL polynucleotide. Selectivity of hybridization exists when hybridization occurs with a certain degree of specificity rather than being random. Typically, selective hybridization will occur when there is at least about 55% homology over a stretch of at least about 14 nucleotides, preferably at least about 65%, more preferably at least about 75%, and most preferably at least about 90%. See, Kanehisa, *Nuc. Acids Res.*, 12:203–213 (1984). The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides. Selective hybridization conditions will be stringent combined conditions of salt, temperature, organic solvents, and other parameters typically controlled in hybridization reactions. Stringent temperature conditions will generally include temperatures in excess of 30° C., typically in excess of 37° C., and preferably in excess of 45° C. Stringent salt conditions will ordinarily be less than 1M, typically less than 500 mM, and preferably less than 200 mM. However, the combination of parameters is much more important than the measure of any single parameter. See, e.g., Wetmur et al., *J. Mol. Biol.*, 31:349–370 (1968).

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032 published May 4, 1988, or via deoxynucleoside H-phosphonate intermediates as described by Froehler et al., *Nucl. Acids Res.*, 14:5399–5407 (1986)). They are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands on the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See, generally, Mullis et al., *Cold Spring Harbor Symp. Quant. Biol.*, 51:263 (1987); Erlich, ed., *PCR Technology*, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer.

Generally, the nomenclature used hereafter and the laboratory procedures in cell culture, molecular genetics, and nucleic acid chemistry described below are those well known and commonly employed in the art. Standard techniques such as described in Sambrook et al., *Molecular Cloning, A Laboratory Manual*, 2nd edition, Cold Spring Harbor Laboratory, Cold Spring Harbor, N.Y. (1989), are used for recombinant nucleic acid methods, polynucleotide synthesis, cell culture, and transgene incorporation, e.g., electroporation, injection, lipofection. Generally enzymatic reactions, oligonucleotide synthesis, and purification steps are performed according to the specifications. The techniques and procedures are generally performed according to conventional methods in the art and various general references which are provided throughout this document. The procedures therein are believed to be well known in the art and are provided for the convenience of the reader.

Specific Embodiments
Polynucleotide and Polypeptide Compositions

The present invention provides an "isolated" polynucleotide encoding a novel, ras p21-interacting protein, defined herein as RGL. The nucleotide and amino acid sequences of RGL, SEQ ID No:1 and SEQ ID NO:2, respectively, are shown in FIG. 1A. The RID nucleotide sequence, SEQ ID NO:3, corresponding to nucleotide positions 1972–2463 shown in FIG. 1A is also provided. SEQ ID NO:4 refers to the RID amino acid sequence encompassing amino acids 605–768. RID is a 164 amino acid domain of the RGL protein that interacts with ras p21. These sequences are also shown in Kikuchi et al. *Mol. Cell. Biol.*, 14:7483–7491 (1994).

Specifically provided by the invention is an isolated polynucleotide comprising at least 80% sequence identity with the nucleotide sequence of SEQ ID NO:1, an allelic or species variation thereof, or a fragment thereof. A polynucleotide comprising the RID sequence of SEQ ID NO:3 is also provided.

The invention also provides certain recombinant DNA molecules comprising the nucleotide sequence of SEQ ID NO:1 or a fragment thereof, such as the pGAD/RID plasmid encoding a RID-GAL4 transactivation domain fusion protein. Another recombination DNA molecule is pGAD/ralGDS, encoding a ralGDS-GAL4 transactivation domain fusion protein. These plasmids/expression vectors are described in the experimental examples below.

Compositions of the RGL polypeptide and derivatives thereof are also provided. These compositions will be full length natural forms, the natural forms including allelic and species variations of the polypeptide encoded by SEQ ID NO:2, fragments of the natural forms, fusion proteins with those fragments and modified forms of each. The compositions include an isolated polypeptide of less than about 200 amino acids, usually about 164 amino acids comprising a ras interacting-domain (RID), this polypeptide referred to as a RID polypeptide and encoded by the sequence of SEQ ID NO:4. In a preferred embodiment, the RGL polypeptide or fragment thereof is capable of binding the effector loop of ras p21. Also provided are particular fusion proteins based on the RGL sequence, such as the RID-GAL4 fusion protein used in the yeast two-hybrid system and described in the experimental examples. In addition, pharmaceutical compositions are provided that include the RGL polypeptide and its derivatives or the RID polypeptide and its derivatives with a pharmaceutically acceptable carrier.

Uses of RGL Polynucleotide

The RGL polynucleotide and fragments thereof have various uses. In one embodiment, the RGL polynucleotide or fragments thereof will be used to prepare expression constructs for RGL. Some of the expression constructs are described in detail under Experimental Examples. The expression vectors will contain the necessary elements for transcription and translation of the DNA fragments into polypeptide if these elements are not already present in the DNA fragments themselves. These necessary elements include a promoter 5' of the DNA insert to be expressed, a transcription and translation initiation site, stop codons, poly-A signal sequence, splice signals. DNA sequences encoding the protein will be operably linked to a promoter appropriate for expression in a particular cell type. Usually a strong promoter will be employed to provide for high level transcription and expression. Examples of strong promoters include human cytomegalovirus promoter. An enhancer may be necessary to function in conjunction with the promoter. The expression construct normally comprises one or more DNA sequences encoding RGL under the transcriptional control of a native or other promoter. Usually the promoter will be a eukaryotic promoter for expression in a mammalian cell, where the mammalian cell may or may not result in the expression of RGL. The selection of an appropriate promoter will depend upon the host, but promoters such as the trp, lac and phage promoters, tRNA promoters and glycolytic enzyme promoters are known. Non-fungal promoters will be preferred where expression occurs in non-fungal cells. occasionally, it might be useful to express the sequences in other types of cells and appropriate promoters may be selected. In some circumstances, an inducible promoter may be preferred. See, e.g., Sambrook et al., *Molecular Cloning: A Laboratory Guide*, Vols. 1–3 (1989), Cold Spring Harbor Press.

Plasmid, viral or YAC vectors are contemplated. Conveniently available expression vectors which include the replication system and transcriptional and translational regulatory sequences together with a polylinker restriction site for insertion of the protein encoding sequence, may be employed. Examples of workable combinations of cell lines and expression vectors are described in Sambrook et al. (1989); see also, Metzger et al. (1988), *Nature* 334:31–36.

It may be desirable to produce the RGL protein or fragments thereof in a prokaryotic host, in which case a prokaryotic promoter is preferred. Examples of prokaryotic promoters are trp, lac, and lambda. See Sambrook et al. (1989) for other useful prokaryotic promoters. Usually a strong promoter will be employed to provide for high level transcription and expression.

The expression construct will often be contained in a vector capable of stable extrachromosomal maintenance in an appropriate cellular host or may be integrated into the host genome. The expression construct may be bordered by sequences which allow for insertion into a host, such as transposon sequences, lysogenic viral sequences, or the like. Normally, markers are provided with the expression construct which allow for selection of host cells containing the construct. The marker is preferably on the same DNA molecule but can be on a different DNA molecule that is cointroduced into the host cell. In prokaryotic cells, markers such as a resistance to a cytotoxic agent, complementation of an auxotrophic host to prototrophy, production of a detectable product, etc., serve the purpose.

The expression construct can be joined to a replication system recognized by the intended host cell. Various replication systems include viral replication systems such as retroviruses, simian virus, bovine papilloma virus, or the like.

While the wild-type sequences of RGL or RID will generally be employed, in some situations one or more mutations or minor modifications may be introduced, such as deletions, substitutions or insertions resulting in changes in the amino acid sequence, providing silent mutations or modifying amino acid residues or amino or carboxyl terminal groups. Conservative amino acid substitutions can be introduced. These amino acid changes can be made using techniques such as PCR or site-directed mutagenesis. There will be circumstances where gene fusions between RGL and another protein can be useful. The fusion proteins will be recombinantly produced. The recombinant nucleic acid sequences used to produce fusion proteins of the present invention will often be derived from natural or synthetic sequences.

The nucleic acid constructs will be useful to introduce into cells, providing an efficient and economical means to produce commercially useful quantities of the protein compositions. Transfected cells producing varying quantities of full length RGL or only the RID fragment will also be useful in evaluating the effect of overexpression of RGL on ras function and transformation. Nucleic acid constructs expressing various lengths and mutant forms of RGL can be used to determine the minimum region involved in the RGL/ras interaction to the specific amino acid contacts.

The means of introduction of the expression construct into a host cell will vary depending upon the particular vector and the target host. Introduction can be achieved by any convenient means, including fusion, conjugation, transfection, transduction, electroporation, injection, or the like. See, e.g., Sambrook, et al. (1989), supra. The DNA expression vectors encoding the active fusion kinase polypeptide are introduced into the appropriate cellular host under conditions which favor expression of the polypeptide and isolation of the resultant expressed polypeptide. This implies using an expression vector compatible with the host cell, the vector containing the necessary elements described above for expression of the polypeptide. The tranfected cells are then provided with the optimum nutrient, gas and temperature conditions for optimal protein production. These conditions will depend on the cell type. Transient or stable transfection procedures can be used.

The host cells will normally be immortalized cells, i.e., cells that can be continuously passaged in culture. For the most part, these cells will be convenient mammalian cell lines which are able to express a RGL protein and, where desirable, process the polypeptide so as to provide an appropriate mature polypeptide. By processing is intended glycosylation, ubiquitination, disulfide bond formation, general post-translational modification, or the like.

A wide variety of both prokaryotic and eukaryotic hosts will be employed for expression of the proteins and peptides. Useful hosts include bacteria, such as *E. coli*, yeast, filamentous fungi, insect cells such as Sf9, mammalian cells, typically immortalized, e.g., various mouse cell lines, monkey cell lines, Chinese hamster ovary cell lines, human cell lines, derivatives of them, or the like. In some cases, the cells will be derived from a neoplastic host cell or wild-type cells will be transformed with oncogenes, tumor causing viruses or the like. Cells carrying the RGL polynucleotide compositions are covered by this invention.

Cells transformed with the polynucleotide compositions can be used to create transgenic mice. Such transgenic mice are useful e.g. to study the effect of overexpression of the RID polypeptide on growth and development of the animal. The procedure for producing transgenic mice is known in the art and are described e.g. in detail in Hogan et al., *Manipulating the Mouse Embryo*, Cold Spring Harbor laboratory, Cold Spring Harbor, N.Y. (1986).

In another aspect of the invention, the mouse full length RGL polynucleotide according to the sequence of SEQ ID NO:1, or fragments thereof will be used to prepare probes to screen DNA libraries to isolate RGL genes or gene fragments encoded by other species, particularly human. The methods of screening DNA libraries are generally well known, see eg. Sambrook et al. (1989). The probes can be from about 50 bp to several kb in length. Preferably, the probe should be free of vector sequences. The probes are typically prepared labeled. Radiolabels such as $^{32}P$ are normally used although non-radioactive labels are also suitable.

Genomic and cDNA libraries prepared from mammalian, insect or yeast cells are included for screening purposes. The DNA libraries may be constructed in phage, bacteria or yeast. Clones that hybridize to the probe are identified such as by autoradiography if radiolabeled probes are used. DNA is isolated from hybridizing clones and analyzed for the presence of RGL gene sequence as verification that the hybridizing clone carries all or part of the RGL gene. The DNA sequence carried by the clone is compared with that of SEQ ID NO:1. The RGL gene or fragment thereof will then be isolated from the vector by restriction endonucleases. It may be necessary to isolate several overlapping DNA sequences from different hybridizing clones to recombinantly reproduce the full length gene in one contiguous DNA fragment.

Alternatively, with the availability of the mouse RGL sequence (FIG. 1A), RGL genes from other species can be isolated by Polymerase Chain Reaction (PCR) by selecting appropriate pairs of primers based on the known sequence and using genomic DNA or cDNA prepared from cells as the template. Primers can be chemically synthesized and will be at least 10 nucleotides in length, more usually 14 nucleotides, preferably 17 nucleotides but can be as long as 100 bp nucleotides. Pairs of primers corresponding to the 5' and 3' ends of the gene or to the internal regions of the gene can be used. Several rounds of PCR may be required to prepare overlapping clones that can then be linked by recombinant methods to produce the entire gene in one DNA fragment.

The invention also provides a method of determining if the RGL gene from a cell of interest is mutated. The cells can be from cultured cell lines or from tissue isolated from an animal or human. For example, cells can be prepared from a human tumor biopsy. PCR can be used to amplify all or part of the RGL gene using selected primers and the amplified DNA fragment sequenced or analyzed for restriction enzyme cleavage patterns. The nucleotide sequence or restriction analysis is compared to the wild type sequence of RGL from the appropriate species. Therefore, the wild type sequence acts as a standard or positive control.

In another aspect, the RGL polynucleotide or oligonucleotides derived from it find use to isolate a gene encoding other members of the RGL/ralGDS family of proteins that binds to ras p21 and that share "substantial homology" with RGL and ralGDS genes. Such ras binding proteins could potentially be effector or regulator proteins of ras. Thus, the invention provides a method of identifying a gene encoding a ras p21-binding protein, by screening a DNA library with a RID probe to identify a hybridizing clone containing a RID sequence, the presence of a RID sequence being indicative of a gene encoding a ras p21-binding protein.

One specific embodiment of the invention is a method of identifying a ras effector loop-binding protein other than RGL. Probes corresponding to the RGL sequence are used to screen a gene library. Library screening has been described above. Preferably, the probes for screening the gene library will comprise oligonucleotides corresponding to the RID sequence of RGL or ralGDS. The entire RID sequence can be used as probe. The probes will be oligonucleotides or DNA fragments having at least about 25 nucleotides, more usually at least about 100 nucleotides, and fewer than about 5 knt (kilonucleotides), usually fewer than about 0.5 knt. The screening of mammalian cDNA or genomic DNA libraries, especially human DNA libraries will be targeted although eukaryotes such as yeast and insects are also of interest for evolutionary comparisons.

A gene that hybridizes with the probe and is determined to be substantially homologous to the RGL gene in nucleotide sequence will be isolated. The homologous gene will be inserted into an appropriate expression vector and introduced into a suitable host for expression to produce the encoded polypeptide. The encoded polypeptide will then be assayed to determine if it binds the effector loop of ras using the same procedure for analyzing the interaction of ralGDS with ras p21, described below in the Experimental Examples. If binding is observed, the polypeptide is determined to be a newly discovered, ras effector loop-binding protein.

The RGL or RID probes can also be used to determine whether RNA encoding RGL or an RGL homolog is present in a cell. This can be done by the procedure of Northern Blotting. In situ hybridization can also be performed on tissue sections of the organism to determine developmental regulation and compare expression levels in various tissues. The probes can be labeled using any suitable labels or tags eg. radiolabel, biotin-avidin. The procedures of preparing probes, Southern blotting, Northern blotting and in situ hybridizations are well known in the art. See, for example, Sambrook et al., 1989.

Conditions for hybridization can be varied. Initially, less stringent conditions can be used. However, if a high background of non-specific hybridization is observed, more stringent conditions will be employed.

The RGL polynucleotide or fragments thereof also find use in the construction of vectors encoding fusion proteins. Fusion proteins encoding RGL fused to the GAL4 DNA binding domain can be used in the yeast two hybrid system to isolate proteins that interact with the RGL protein. This method allows the isolation of the cloned genes for the interacting proteins and eventually the identification of the interacting proteins. Knowledge of the interacting proteins in the ras signaling pathway will allow the screening of drugs for agonists and antagonists of ras dependent cell proliferation and differentiation. The yeast two-hybrid system is described above and in the experimental examples. The RID sequence in particular is suitable for fusing to the GAL4 DNA binding domain. The second fusion protein will be encoded by a cDNA library linked to the GAL4 transactivation domain. A yeast reporter strain is then cotransformed with plasmids encoding both fusion proteins.

Isolation of RGL and RID PolyPeptide

The RGL polypeptide can be isolated from a normally expressing cell or a transfected cell by immunoprecipitation or affinity chromatography of cell lysates using RGL-specific antibody. The antibody can be in solution or affixed on a solid substrate. It may be more efficient to isolate the protein from transfected cells that may produce larger quantities of the protein due to particular characteristics of the expression construct, such as a strong promoter. The Experimental Examples describe purification of ralGDS from the cytosolic fraction of transfected Sf9 insect cells. The RGL protein can be similarly expressed and purified. Instead of or in addition to immunological methods, the peptide will generally be isolated by techniques employing FPLC, HPLC, electrophoresis, gradient centrifugation and other methods routinely used in protein purification to provide a substantially pure product, i.e., particularly free of cellular contaminants. For protein purification methods, see, e.g., Jacoby, *Methods in Enzymology*, Vol. 104 (1984), Academic Press, New York; Scopes, *Protein Purification: Principles and Practice*, (2nd Ed.) (1987) Springer-Verlag, New York; Deutscher (ed.), *Guide to Protein Purification, Methods in Enzymology*, Vol. 182 (1990).

Uses of RGL Polypeptide Compositions

The RGL polypeptide compositions find several uses. The polypeptide compositions of RGL and RID are useful for raising antibodies, both polyclonal and monoclonal. Such antibodies are powerful tools that can be employed in various assays and diagnostic situations particularly where immunoprecipitation, immunoblotting and affinity purification procedures are necessary. Thus, one object of the invention is to provide antibodies that specifically binds to the RGL polypeptide comprising the sequence of SEQ ID NO:2, an allelic or species variation thereof, or a fragment thereof. Antibodies that bind just the RID encoded by SEQ ID NO:4 are included. The invention also provides hybridoma lines that produce monoclonal antibodies to the RGL polypeptide.

These antibodies find use in isolating the RGL protein and any structurally related proteins expressing an epitope recognized by the anti-RGL antibody. Isolation of RCL and structurally related proteins can be accomplished by simply immunoprecipitating the proteins from lysates of normally expressing or transfected cells. Alternatively, affinity purification of eg. cell lysates can be performed using the RGL antibody fixed on a solid matrix such as a column of beads or a filter paper.

RGL antibodies are also useful to study the interaction of RGL with ras in vivo in normal and growth disregulated or cancerous cells. The same protocol described in the experimental examples for studying the interaction of ralGDS with ras p21 in intact cells can be followed. Antibodies capable of specifically binding RID or otherwise blocking the binding of RGL to ras are desirable reagents.

Thirdly, the RGL specific antibodies find use in isolating any RGL-associating protein that co-immunoprecipitate with RGL. RGL-associating proteins are useful to study the downstream effectors of ras and the regulation of ras and RGL function.

In a different aspect, RGL specific antibodies can serve as a diagnostic reagents to detect deficiencies in RGL such as expression levels in tumor cells from cancer patients, particularly in cases of bladder and colon cancers.

Polyclonal and/or monoclonal antibodies with specificity to RGL can be prepared by in vitro or in vivo techniques following standard procedures as described in, e.g., Harlow, et al., *Antibodies: A Laboratory Manual* (1988), Cold Spring Harbor Press, New York. Antibodies are produced by immunizing an appropriate vertebrate host, e.g., rabbit or rodents, with the entire RGL protein or peptides derived thereof, or in conjunction with an adjuvant. Usually two or more immunizations will be involved, and the blood or spleen will be harvested a few days after the last injection.

For immunization, preferably peptides corresponding to regions of the protein comprising hydrophilic residues or residues exposed to the aqueous phase are selected. Immunogens comprising the entire RID polypeptide (SEQ ID NO:4) or peptide derivatives thereof are also desirable. Synthetic peptide fragments may be prepared in a peptide synthesizer and coupled to a carrier molecule (e.g., keyhole limpet hemocyanin) and the conjugate injected into rabbits at selected times over several months.

For production of polyclonal antibodies, an appropriate target immune system is selected, typically a rabbit or a mouse. The substantially purified antigen is presented to the immune system in a fashion determined by methods appropriate for the animal and other parameters well known to immunologists. Typical sites for injection are in the footpads, intramuscularly, intraperitoneally, or intradermally. Of course, another species will sometimes be substituted for a mouse or rabbit, including goats, sheep, cows, guinea pigs, and rats.

The rabbit sera is tested for immunoreactivity to the RGL protein or peptide immunogen by an immunoassay, typically with preimmune sera as one of the negative controls. The immunoassay can be a radioimmunoassay, an enzyme-linked assay (ELISA), a fluorescent assay, or any of many other choices, most of which are functionally equivalent but may exhibit advantages under specific conditions. The polyclonal antibodies can be provided commercially in the form of antisera or in purified form. From the polyclonal antisera, the immunoglobulins may be precipitated, isolated and purified, such as by affinity purification. Preferably, the purified form is substantially free of non-specific antibodies and cellular contaminants.

Monoclonal antibodies with affinities of $10^8$ $M^{-1}$ preferably $10^9$ to $10^{10}$, or stronger will typically be made by standard procedures as described, e.g., in Harlow et al., *Antibodies: A Laboratory Manual*, CSH Laboratory (1988); or Goding, *Monoclonal Antibodies: Principles and Practice* (2d ed) (1986), Academic Press, New York. Normally, mice are used to produce monoclonal antibodies although rats, guinea pigs and other animals can also be used. After the appropriate period of time from the immunization schedule, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen.

Other suitable techniques involve in vitro exposure of lymphocytes to the antigenic polypeptides or alternatively to selection of libraries of antibodies in phage or similar vectors. See, Huse et al., "Generation of a Large Combinatorial Library of the Immunoglobulin Repertoire in Phage Lambda," *Science* 246:1275–1281 (1989).

The polypeptides and antibodies of the present invention may be used with or without modification. Frequently, the polypeptides and antibodies will be labeled by conjugating, either covalently or non-covalently, a substance which provides for a detectable signal.

A wide variety of labels and conjugation techniques are-known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

The RGL antibodies of the invention can also be provided in a kit for use in any of the various applications described above. The contents of the kit will vary depending on the intended application of the antibody and may include other reagents and instructions for the use of the antibody preparation and the reagents. At least one aliquot of the antibody will be provided. Different RGL antibodies with specificities for different regions of the protein can be provided. Different antibodies may be desirable for verification of an assay result. The aliquots can be contained in any suitable container such as a vial or a tube. The polyclonal antibody can be in the form of antisera or affinity purified. Monoclonal antibodies can be provided in the form of ascites, culture media or a buffer such as phosphate buffered saline solution. The antibody preparation can be provided in solution or in lyophilized form, and may even be immobilized on a substrate such as a column matrix. The antibody preparation may also contain in it preservatives such as sodium azide or protease inhibitors such as EDTA. A carrier protein such as BSA or ovalbumin, usually between 0.55%–5%, may be included for stability. The solution form of the antibody, especially the purified form, may contain up to 50% glycerol if the kit is to be stored frozen at −20° C. to −70° C. If the antibody is provided in lyophilized form, the kit can include a reconstitution buffer to reconstitute the antibody.

If the antibody is to be used in western blotting, reagents for use in the blotting procedure can be included in the kit. A secondary, labeled antibody capable of binding to the RGL antibody allowing detection of the binding, can be included. The labeled antibody may be conjugated to an enzyme such as alkaline phosphatase or horse radish peroxidase.

Since the RID of RGL binds ras, the RGL polypeptide or the RID polypeptide is useful in the isolation of any RGL interacting protein including ras p21.

Thus, the invention also provides a method of isolating a RGL interacting protein. The method comprises contacting a cell lysate suspected of containing a RGL interacting protein with a RGL polypeptide and isolating any protein bound to said RGL polypeptide as a RGL interacting protein.

One embodiment of the method, an RGL polypeptide is immobilized on a solid matrix. If the isolation of ras p21 is desired, it is preferable that an immobilized RID polypeptide be used. The solid matrix can comprise various materials such as is commonly used in column chromatography, including sepharose, sephadex, agarose, polystyrene and latex beads. The solid matrix can also be filter paper or membrane, such as nitrocellulose and polyvinylidene fluoride (PVDF) membrane. The RGL polypeptide can be coupled to the solid matrix directly or indirectly. Direct methods include covalent coupling to sepharose beads using cyanogen bromide. Indirect coupling can take advantage of an RGL antibody or some other moiety suitable for linking the two components such as biotin-avidin binding pairs. RGL or RID fusion proteins may be more conveniently immobilized if the fusion protein can bind a ligand provided on the matrix.

Lysates are produced from cells that normally express RGL. Cell lysates will be contacted with the immobilized RGL polypeptide such as by running the lysates over an RGL affinity column to allow any RGL interacting protein to bind the immobilized RGL polypeptide under optimum conditions. Preferably the binding reaction is carried out between 4° C. and normal physiological temperature. Buffer conditions can be modified to favor capture of this binding. For example, the pH and salt conditions can be varied. The matrix is then washed with buffer to remove any unbound or nonspecifically bound cellular components. Any protein that bound to the RGL polypeptide will be isolated by elution off the solid matrix such as by using a salt gradient or using soluble RGL polypeptide and fragments thereof to compete for binding.

RGL fusion proteins find particular use in the yeast two hybrid system to isolate RGL interacting proteins as described earlier. Peptide expression libraries such as by phage display methodology, can be screened for ligand binding to the RGL polypeptide or fragments thereof or fusion proteins thereof.

RGL or RGL fusion proteins also find use to detect RGL-interacting proteins by Western blotting, using the RGL protein in solution to bind protein bands on the blot and detecting the bound RGL. In this circumstance, the RGL protein can be labeled directly or indirectly. Indirect labeling will include eg. a labeled antibody binding to RGL.

RGL or RID can be fused, e.g., with glutathione-S-transferase (GST), to produce GST-RGL or GST-RID fusion proteins. Expression vectors carrying GST sequence and specifically constructed to facilitate recombinantly producing GST fusion proteins are commercially available from most sources that supply cloning vectors. The fusion proteins may also comprise RGL or fragments thereof fused to the product or polypeptide encoded by a second gene. A product encoded by only a portion or a fragment of the second gene instead of the entire gene, may be sufficient. For example, RGL or a fragment thereof may be fused to a second gene such as the *E. coli* lacZ gene that will allow detection of expression. Other convenient fusion proteins will comprise RGL or RID sequence or portions thereof linked to a tag.

In constructing fusion proteins, it will be understood that the amino or carboxy terminus of the RGL protein, or wherever the fusion junction is, may be modified to facilitate cloning or for other reasons eg. to allow cleavage of the fusion protein and release of the separate portions.

The tag can be a label or some means that allows identification of the fusion protein. The tag is introduced into a site in the polypeptide that will not interfere with the folding and the function of the protein, generally at the N- or the C-terminus. The tag can be an epitope tag recognizable by an antibody, a member of a binding pair, an enzyme or any other suitable entity. The tag can be a cleavable sequence such as the phosphatidylinositol-glycan (PIG) signal sequence present in proteins such as alkaline phosphatase, DAF and acetylcholinesterase. The PIG sequence is cleavable by the enzyme phosphatidylinositol phospholipase C (PI-PLC) (Ferguson, *Ann. Rev. Biochem.*, 57:285–320 (1988)). The influenza virus hemagglutinin (HA) and the myc (10 amino acid-EQKLISEEDL) epitopes are particularly useful tags. Examples of binding pairs are ligand-receptor, antigen-antibody and small molecules like avidin-biotin. Enzyme tags include horse radish peroxidase, alkaline phosphatase and β-galactosidase which can act on a substrate to produce a color signal. For example, the protein can be fused to an epitope tag recognizable by an available antibody. The antibody to the tag is useful eg. to immobilize the RGL protein on an affinity column or to detect the protein such as when the fusion protein is used in Western blotting.

The invention also provides a method to block or modulate ras p21 activity in vitro and in vivo using the RID polypeptide. The binding of RID to the effector loop of ras p21 prevents the GTP-bound active form of ras p21 from interacting with effector proteins that bind at the same site of ras. These effector proteins mediate ras p21-dependent processes such as growth factor-stimulated or oncogene-induced cell proliferation. Various medical conditions are attributed to a disregulation in ras activity, i.e., ras dysfunction. Mutated ras can result in uncontrolled proliferation leading to cancer, e.g., lung, bladder, and colon carcinoma.

The RID polypeptide derived from either the RGL protein or the ralGDS protein will generally be effective in modifying the extent to which ras disregulates cell proliferation, differentiation and other ras dependent processes, this modification being implied when the term "modulating ras p21 activity" is used herein. By competing for binding to the ras effector loop, the RID polypeptide will block or reduce the ability of active GTP-bound ras p21 to interact with downstream effector proteins such as PI(3)K, Raf, neurofibromatosis gene product (NF1) and GAP proteins including ras-GAP and neurofibromin. This, in turn, will affect the cellular signalling events downstream of ras p21. For example, blocking the binding of GAP to ras could increase the amount of ras bound in the GTP-bound active state upon cell stimulation.

The method of blocking ras p21 activity comprises providing a RID polypeptide in a cell expressing ras p21 protein wherein the RID polypeptide will bind to said ras p21 protein to block ras p21 activity. The RID polypeptide itself can be directly introduced into the cell under study where arrest or modulation of ras function is desired. Methods of introducing the RID polypeptide into the cell include microinjection of the isolated polypeptide (expressed in other cells) or the use of appropriate drug delivery vehicles such as liposomes to deliver the polypeptide.

Alternatively, the RID polypeptide can be provided by introducing an expression construct encoding the RID polypeptide into an affected ras expressing cell wherein the RID polypeptide will be expressed in an amount effective to interfere with ras p21 activity and thus inhibit proliferation. Expression constructs can be targeted to a particular cells by using nucleic acid delivery vehicles that contain targeting moieties on the surface of the vehicle. Examples of such vehicles include liposomes or recombinant viruses expressing receptors for cell surface markers. In some circumstances, complete blockage of ras activity may require high level expression i.e. overexpression of the RID polypeptide for effective competition. In that circumstance, the expression construct can be designed to contain the necessary elements such as strong promoters, inducible promoters and enhancers to achieve high level expression of the RID polypeptide. The RID polypeptide expressed intracellularly will be contacted with and bind to the ras p21 protein.

The method of modifying ras p21 activity in vivo can be applied to alleviating a patient suffering from a cell proliferative condition such as cancer. The method comprises administering to the patient, a therapeutically effective amount of a pharmaceutical composition comprising a RID polypeptide, and a pharmaceutically acceptable carrier. The RID polypeptide will be specifically targeted to the affected cells, such cells being tumor cells in the case of cancer, and cells of the cardiac valve in restenosis. Another pharmaceutical composition for use in the treatment method will comprise an expression vector suitable for introduction into and expression of a therapeutically effective amount of a RID polypeptide in, cancer and other affected cells.

Drug delivery vehicles such as liposomes, can be used to deliver and provide sustained release of the formulations in the body. The liposomes can have targeting moieties exposed on the surface such as antibodies, ligands or receptors to specific cell surface molecules. For example, it may be desirable to limit the delivery of the formulation to only tumor cells. Such cells can be targeted to receive the therapeutic formulation by incorporating into the liposome carrier, a targeting moiety that recognizes and binds a specific tumor surface marker. Liposome drug delivery is known in the art (see, e.g., *Biochimica et Biophysica Acta* 113:201–227 (1992)).

The quantities of reagents determined to be an effective amount for treatment will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds), *Goodman and Gilman's: The Pharmacological Bases of Therapeutics*, 8th Ed. (1990), Pergamon Press; and *Remington's Pharmaceutical Sciences*, 17th Ed. (1990), Mack Publishing Co., Easton, Pa. Methods for administration are discussed therein, e.g., for oral, intravenous, intraperitoneal, or intramuscular administration, transdermal diffusion, and others.

The pharmaceutical compositions will be administered by intravenous, parenteral, intraperitoneal, intramuscular, oral, or local administration, such as by aerosol or transdermally, for therapeutic treatment. The pharmaceutical compositions can be administered in a variety of unit dosage forms depending upon the method of administration. For example, unit dosage forms suitable for oral administration include powder, tablets, pills, capsules and dragees.

The pharmaceutical compositions will often be administered intravenously. Thus, this invention provides compositions for intravenous administration which comprise a solution of the polypeptide dissolved or suspended in an acceptable carrier, preferably an aqueous carrier. Slow release formulations, or slow release delivery vehicles will often be utilized for continuous administration. "Pharmaceutically acceptable carriers" will include water, saline, buffers, and other compounds described, e.g., in the Merck Index, Merck & Co., Rahway, N.J. These compositions will sometimes be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, preferably about 20% (see, Remington's, supra).

The compositions containing the compounds can be administered for prophylactic and/or therapeutic treatments. In therapeutic applications, compositions are administered to a patient already suffering from a disease, as described above, in an amount sufficient to cure or at least alleviate the symptoms of the disease and its complications. An amount adequate to accomplish this is defined as "therapeutically effective dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight.

EXPERIMENTAL EXAMPLES

The following examples are by way of illustration and are not meant to be construed as a limitation on the scope of the invention.

Materials and Methods

Materials and Chemicals.

PC62 and the PC51/mouse embryonic cDNA library were provided by P. M. Chevray and D. Nathans (Johns Hopkins University, Baltimore, Md.) (Chevray et al., *Proc. Natl. Acad. Sci. USA*, 89:5789–5793 (1992)). PC62 contains an ADH promoter expressing the GAL4 DNA-binding domain (amino acids 1 to 147), and PC51 contains the ADH promoter expressing the GAL4 transactivation domain (amino acids 768 to 881). The ralGDSb and ralB p24 cDNAs and the anti-ralGDS antibody were provided by B. W. Giddings, C. F. Albright, and R. A. Weinberg (Whitehead Institute for Biomedical Research, Cambridge, Mass.) (Albright et al., *EMBO J.*, 12:339–347 (1993)). The c-H-ras p21 cDNA, dominant negative ras p21 cDNA (ras p21$^{S17N}$ [a form of ras p21 in which Ser-17 is changed to Asn]), and the hybridoma cells producing anti-ras p21 antibody (Y13-259) were provided by J. Downward (Imperial Cancer Research Institute, London, England). pGBT9, pGBT/ras p21, and pGBT/rap1 p21 were provided by L. Van Aelst and M. Wigler (Cold Spring Harbor Laboratory, Cold Spring Harbor, N.Y.) (Van Aelst et al., *Proc. Natl. Acad. Sci. USA*, 90:6213–6217 (1993)). *S. cerevisiae* YPB2 and pGAD were provided by G. Hannon and D. Beach (Cold Spring Harbor Laboratory, Cold Spring Harbor, N.Y.). *S. cerevisiae* Y153 was provided by S. Field (University of California, Berkeley) (Durfee et al., *Genes Dev.*, 7:555–569 (1993). rac1 p21$^{G12V}$ (a form of rac1 p21 in which Gly-12 is changed to Val) was provided by Alan Hall (Institute of Cancer Research, London, England). The neurofibromatosis 1 (NF1) cDNA was provided by G. Xu (University of Utah, Salt Lake City) (Xu et al., *Cell*, 63:835–841 (1990)). *Spodoptera frugiperda* (Sf9) cells, pVL1393, and BaculoGold linearized baculovirus DNA were purchased from Pharmingen (San Diego, Calif.). High-five cells were from Invitrogen (San Diego, Calif.). The anti-ras p21 antibodies (Y13-238 for immunoprecipitation assay and F235 for immunoblot analysis) were from Oncogene Science Inc. (New York, N.Y.). [γ-$^{32}$P]GTP and [α-$^{32}$P]GTP were from DuPont NEN Research Product (Boston, Mass.). All procedures of passage, infection, and transfection of Sf9 cells and the isolation of recombinant baculoviruses were carried out as described previously (Summers et al., 1987, A manual of methods for baculovirus vectors and insect cell culture procedures. Texas Agricultural Experiment Station, College Station). c-ras p21 and ralGDS were purified from the cytosolic fraction of Sf9 cells and High-five cells, respectively, as described previously (Albright, supra; Mizuno et al., *Proc. Natl. Acad. Sci. USA*, 88:6442–6446 (1991)). Glutathione S-transferase (GST) fused to the N-terminal region of Raf (amino acids 1 to 322) (GST-N-Raf) and GST fused to the NF1 catalytic domain (GST-NF1) were purified from Sf9 cells expressing GST-N-Raf and *Escherichia coli* expressing GST-NF1, respectively, as described previously (Kikuchi et al., *J. Biol. Chem.*, 269:20054–20059 (1994); Xu, supra).

Plasmid Descriptions and Construction.

PC51/mouse embryonic cDNA library contains the ADH promoter expressing the GAL4 transactivation domain (amino acids 768 to 881).

pGAD contains the ADH promoter expressing the GAL4 transactivation domain (amino acids 768 to 881).

pGAD/RID

To make PGAD encoding the ras p21-interacting domain (RID) of RGL (amino acids 605 to 768), 0.5-kb fragment containing RID with BamHI and SalI sites was synthesized by PCR. This fragment was digested with BamHI and SalI and inserted into BamHI- and SalI-cut pGAD to generate pGAD/RID.

pGAD/ralGDS

To construct pGAD containing ralGDS, pBluescript KS/ralGDS was digested with NCOI. The 1.8-kb fragment which represents the N-terminal two-thirds of ralGDS (N-ralGDS) was blunted with Klenow enzyme and inserted into pGAD which was digested with SmaI to generate pGAD/N-ralGDS. Then pEV55/ralGDS was digested with AvrII and EcoRI, and the 1.1-kb fragment, which represents the C terminus of ralGDS, was inserted into AvrII-and EcoRI-cut pGAD/N-ralGDS to generated pGAD/ralGDS.

PC62 contains an ADH promoter expressing the GAL4 DNA-binding domain (amino acids 1 to 147).

PC62/ras p21

To construct PC62 encoding c-H-ras p21, the 0.6-kb fragment containing c-H-ras p21 with the SalI site upstream from the initiator methionine codon and the BamHI site downstream from the termination codon was synthesized by PCR. This fragment was digested with SailI and BamHI and inserted into SalI- and BamHI-cut PC62 to generate PC62/ras p21.

ras P21$^{C186S}$ is a form of ras p21 in which Cys-186 is changed to Ser. This mutant is not posttranslationally modified (Hancock et al., Cell 57:1167–1177 (1989)).

ras p21$^{T35A}$ is a form of ras p21 in which Thr-35 is changed to Ala resulting in an effector loop mutant. Both ras P21$^{C186S}$ and ras p21$^{T35A}$ were made by PCR.

pGBT9 contains an ADH promoter expressing the GAL4 DNA-binding domain (amino acids 1 to 147).

pGBT/ras p21$^{C186S}$ and pGBT/ras p21$^{T35A}$

To construct pGBT9 encoding ras p21$^{C186S}$ and ras p21$^{T35A}$, the 0.6-kb fragments containing ras P21$^{C186S}$ and ras p21$^{T35A}$ with SmaI and BamHI sites were synthesized by PCR. These fragments were digested with SmaI and BamHI and inserted into SmaI- and BamHI-cut pGBT9 to generate pGBT/ras p21$^{C186S}$ and pGBT/ras p21$^{T35A}$. To construct pGBT9/ras p21$^{C186S}$ and pGBT/ras p21$^{T35A}$.

pGBT/ralB p24 and pGBT/rac1 p21$^{G12V}$

To construct pGBT9 encoding ralB p24 and rac1 p21$^{G12V}$, the 0.6-kb fragments containing ralB p24 and rac1 p21$^{G12V}$ with BamHI and SalI sites were synthesized by PCR. These fragments were digested with BamHI and SalI and inserted into BamHI- and SalI-cut pGBT9 to generate pGBT/ralB p24 and pGBT/rac1 p21$^{G12V}$ pVL1393/c-ras p21 and pVL1393/ras p21$^{S17N}$ To construct pVL1393 encoding c-ras p21 and ras p21$^{S17N}$, the 0.6-kb fragments containing c-ras p21 and ras p21$^{S17N}$ with BamHI and PstI sites were synthesized by PCR. These fragments were digested with BamHI and PstI and inserted into BamHI- and PstI-cut pVL1393.

Constructions of v-ras p21 (a form of ras p21 in which Gly-12 is changed to Val) and the N-terminal region of Raf in pVL1393 and pV-IKS were carried out as described previously (Kikuchi et al., supra).

Two-hybrid Screening.

The yeast reporter strain YPB2 was cotransformed with PC62/ras p21 and the PC51/mouse embryonic cDNA library and plated at a density of 2.5×10$^4$ colonies per plate on synthetic minimal media lacking histidine, leucine, and tryptophan and supplemented with 30 mM 3-aminotriazole. The plates were incubated for 4 days at 30° C. Of the 0.5 million colonies that were plated, approximately 200 grew in the absence of histidine. These colonies were patched to selective plates and assayed for β-galactosidase activity by a filter assay (Breeden et al., Cold Spring Harbor Symp. Quant. Biol., 50:643–650 (1985)). Eight colonies were positive. Of these, five were specific for PC62/ras p21 when tested with PC62/SH3 domain of mouse p85 (amino acids number 1 to 100). Library inserts from these five colonies were sequenced by using a Promega Sequenase kit (Promega Corporation, Madison, Wis.) after subcloning the inserts as SalI-NotI fragments into pBluescript KS. cDNAs from five colonies had the same orientation, and both strands of these cDNAs were determined. To identify the full-length cDNA of RGL, a probe was made by using the SalI-NotI fragment with a Quick Prime kit (Pharmacia Biotechnology, Piscataway, N.J.) and used to screen a BALB/c3T3 fibroblast cDNA library as described previously (Klippel et al., Mol. Cell. Biol., 14:2675–2685 (1994)).

Interaction Assay of RID or ralGDS with ras p21 and other Small G Proteins in the Yeast Two-Hybrid System.

The yeast reporter strain Y153 (Durfee et al., supra) was cotransformed with pGAD/RID or pGAD/ralGDS and the indicated plasmids and plated on synthetic minimal medium lacking leucine and tryptophan. Plates were incubated for 3 days at 30° C. and assayed for β-galactosidase activity by filter assay (Breeden et al., supra).

Interaction Assay of ralGDS and ras p21 in vivo.

Monolayers of Sf9 cells (2×10$^7$ cells) were infected singly or doubly with high-titer recombinant baculoviruses (10$^8$ PFU/ml) at a multiplicity of infection of 5 per cell. At 72 h postinfection, the cells were washed with cold phosphate-buffered saline and lysed in 1 ml of lysis buffer (20 mM Tris-HCl [pH 7.5], 1% Nonidet P-40, 137 mM NaCl, 10% glycerol, 1 mM phenylmethylsulfonyl fluoride, 20 $\mu$g of aprotinin per ml, 10 $\mu$g of leupeptin per ml) at 4° C. for 1 h. Insoluble material was removed by centrifugation at 4° C. for 30 min at 13,000×g, and 0.2 ml of lysate (0.24 mg of protein) was used for each assay. The lysates expressing ralGDS and v-ras p21 or ras p21$^{S17N}$ were prepared, and the proteins of the lysates were immunoprecipitated with the anti-ras p21 antibody. Y13-238 was used in the immunoprecipitation experiments except that Y13-259 was used for FIG. 2D. The immunoprecipitates were washed once with lysis buffer, twice with 100 mM Tris-HCl (pH 7.5) and 0.5M LiCl, and once with 10 mM Tris-HCl (pH 7.5). The precipitates were subjected to sodium dodecyl sulfate-polyacrylamide gel electrophoresis (SDS-PAGE) (12% polyacrylamide gel) (Laemmli, Nature (London), 227:680–685 (1970)), transferred to nitrocellulose filters, and probed with the anti-ralGDS or anti-ras p21 antibody.

Interaction Assay of ralGDS and ras p21 in vitro.

To make the guanosine 5'-(3-O-thio)triphosphate (GTPγS)- or GDP-bound form of ras p21, c-ras p21 (20 pmol) was incubated for 10 min at 30° C. with 25 $\mu$M GTPγS or GDP in 40 $\mu$l of reaction mixture (20 mM Tris-HCl [pH 7.5], 10 mM EDTA, 5 mM MgCl$_2$, 1 mM dithiothreitol [DTT]. After the incubation, 600 mM MgCl$_2$ was added at a final concentration of 15 mM. The GTPγS- or GDP-bound form of ras p21 was incubated for 30 min at 4° C. with ralGDS (20 pmol) in 80 $\mu$l of reaction mixture (20 mM Tris-HCl [pH 7.5], 5 mM EDTA, 10 mM MgCl$_2$, 0.5 mM DTT, 25 $\mu$M GTPγS or GDP). Then, the anti-ras p21 antibody (Y13-238) was added to this mixture, and the mixture was subjected to immunoprecipitation. The precipitate was subjected to SDS-PAGE, transferred to nitrocellulose filters, and probed with the anti-ralGDS antibody.

GAP Assay of NF1.

The GAP assay for c-ras p21 was performed as described previously (Gibbs et al., Proc. Natl. Acad. Sci. USA, 85:5026–5030 (1988)). Briefly, c-H-ras p21 (2.5 pmol) was preincubated for 5 min at 30° C. in 5 $\mu$l of preincubation mixture (100 mM sodium phosphate [pH 6.8], 0.5 mM EDTA, 0.5 mg of bovine serum albumin per ml, 0.5 mM DTT, 0.5 $\mu$M [γ-$^{32}$P]GTP [20,000 to 30,000 cpm/pmol]). To this preincubation mixture, 45 μl of reaction mixture (500 μM GTP, 22.2 mM sodium N-2-hydroxyethylpiperazine-N'-2-ethanesulfonic acid [HEPES; pH 7.5], 1.1 mM MgCl$_2$, 1.1 mg of bovine serum albumin per ml, 0.11 mM DTT, 2.2 mM Tris-HCl [pH 7.5]) containing 10 nM GST-NF1 and the indicated amounts of ralGDS or GST-N-Raf was added, and a second incubation was performed at 24° C. Assays were quantified by rapid filtration on nitrocellulose filters. GAP activity was calculated from the decrease of the radioactivity of [γ-$^{32}$P]GTP compared with a reaction performed in the absence of GST-NF1, and GAP inhibition activity was expressed as percent decrease of GAP activity of GST-NF1.

Interaction Assay of Raf and ras p21.

To make the [α-$^{32}$P]GTP-bound form of ras p21, c-H-ras p21 (2.5 pmol) was preincubated for 15 min at 30° C. in 5 μl of the preincubation mixture described above except that [α-$^{32}$P]GTP was used instead of [γ-$^{32}$P]GTP. To the preincubation mixture, 45 μl of the reaction mixture described above containing 20 mM GST-N-Raf and the indicated amounts of ralGDS was added, and a second incubation was performed for 30 min at 4° C. GST-N-Raf was precipitated with glutathione-Sepharose 4B, the precipitates were washed, and the remaining radioactivity was counted.

Other Assays.

Protein concentrations were determined with bovine serum albumin as a standard using the Bradford assay (Bradford, *Anal. Biochem.*, 72:248–254 (1976)).

Nucleotide Sequence Accession Number.

The GenBank accession number for the mouse RGL cDNA sequence is U14103.

Results

Isolation of a Protein which Interacts with ras p21 in the Yeast Two-Hybrid System.

To identify proteins that physically interact with H-ras p21, plasmid PC62/ras p21 encoding a fusion protein of ras p21 and the GAL4 DNA-binding domain was cotransformed with a mouse embryonic cDNA library expressed as a fusion with the GAL4 transactivation domain (PC51/mouse embryonic cDNA) into a yeast reporter strain YPB2 carrying the GAL4 binding sites upstream of both the *S. cerevisiae* HIS3 gene and the *E. coli* lacZ gene.

Of the 0.5 million yeast transformants, five grew in the absence of histidine and expressed β-galactosidase activity in a ras p21-dependent manner. The cDNA inserts from these five all encoded a single sequence containing an open reading frame of 164 amino acids and the consensus sequence for a stop codon and polyadenylation. This ras p21-interacting domain was termed RID.

Characterization of RID.

To characterize RID, the association of RID with ras p21 mutants and other small G proteins was examined in the yeast two-hybrid system (Table 1). As assessed by filter assays of β-galactosidase, RID interacted with ras p21. To examine the effect of posttranslational modification of ras p21 on its interaction with RID, ras p21$^{C186S}$ was used. It is known that this mutant is not posttranslationally modified (Hancock et al., *Cell*, 57:1167–1177 (1989)).

Coexpression of RID with ras p21$^{C186S}$ reconstituted β-galactosidase activity. However, RID did not interact with the effector loop mutant of ras p21$^{T35A}$. These findings indicate that the posttranslational modification of ras p21 is not necessary for its binding to RID and that the effector loop of ras p21 is required. Also examined was the specificity of small G proteins which interact with RID. RID interacted with rap1 p21 as well as with ras p21 but not with ralB p24 or with rac p21$^{G12V}$. rap1 p21 is known to have the same effector loop as ras p21 and to associate with the same effector-loop binding protein as ras p21.

TABLE 1

Interaction of RID with ras p21 in the yeast two-hybrid system[a]

| GAL4 DNA-binding domain fusion | GAL4 transactivation domain fusion | β-Galactosidase activity |
|---|---|---|
| Vector | RID | – |
| ras p21 | Vector | – |
| ras p21 | RID | + |
| ras p21$^{C186S}$ | RID | + |
| ras p21$^{T35A}$ | RID | – |
| rap1 p21 | RID | + |
| ralB p24 | RID | – |
| rac1 p21$^{G12V}$ | RID | – |

[a]Y153 was cotransformed with RID and ras p21 mutants or other small G proteins and assayed for β-galactosidase activity. A blue signal, representing β-galactosidase activity, is indicated by a +, and a white signal, indicating a lack of β-galactosidase activity, is shown as a –. In each case, β-galactosidase expression was not detected when cells were transformed with the DNA-binding domain (amino acids 1 to 147) or the transactivation domain (amino acids 768 to 881) fusion alone.

Molecular Cloning of RGL.

Using RID to probe a BALB/c3T3 fibroblast cDNA library, a 2.7-kb cDNA containing an open reading frame of 768 amino acids (FIG. 1A) was identified. The predicted protein sequence had 69% amino acid homology with ralGDS, which is a GDP/GTP exchange protein for ral p24, a member of small G-protein superfamily (FIG. 1B) (Albright et al., supra). This protein was designated RGL. In the RGL cDNA, the 5' noncoding region was long and had a high percentage of G.C base pairs, which is typical in the 5' noncoding region. The neighboring sequence of the first ATG was consistent with the translation initiation start proposed by Kozak (Kozak, *Nucleic Acids Res.*, 15:8125–8148 (1987)).

The sequence of 290 amino acids (amino acids 210 to 499) of RGL was similar to a comparable region of CDC25, which is a GDP/GTP exchange protein for ras p21 (Lowy et al., *Annu. Rev. Biochem.*, 62:851–891 (1993); Martegani et al., *EMBO J.*, 11:2151–2157 (1992)) (FIG. 1C). It is known that this region of CDC25 is important for GDS activity (Albright et al., supra; Lowy and Willumsen, supra; Martegani, supra). RGL and ralGDS had an additional extensive region C terminal to the CDC25-like domain (Albright, supra). RID was located in this region of RGL. There was a region exhibiting 66% amino acid homology with RID in the C terminus of ralGDS. This strong homology in the overall sequence suggests that ralGDS and RGL constitute a family. Furthermore, this structural analysis suggests that ralGDS and RGL may interact with the effector loop of ras p21. Since ralGDS has been well characterized (Albright, supra), it was convenient for testing as to whether it could be an effector protein of ras p21.

Interaction of ralGDS with ras p21 in the Yeast Two-Hybrid System.

Whether ralGDS interacts with ras p21 in the yeast two-hybrid system was examined (Table 2). As assessed by filter assays of β-galactosidase, ralGDS interacted with ras p21. Consistent with the data shown in Table 1, ralGDS interacted with ras p21$^{C186S}$ but not with ras p21$^{T35A}$. Furthermore, ralGDS interacted with rapi p21 as well as with ras p21 but not with ralB p24 or with rac1 p21$^{G12V}$.

Interaction of ralGDS with ras p21 in Intact Cells.

Figures 2A, 2B, 2C, 2D:
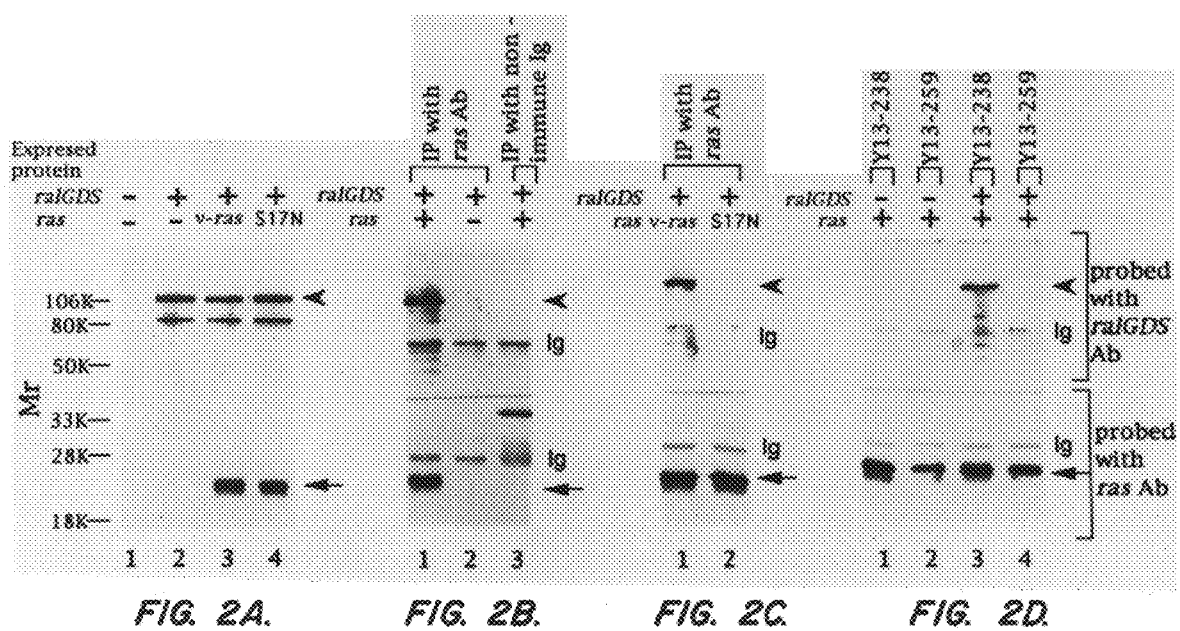
FIG. 2A shows coexpression of ralGDS with ras p21 in Sf9 cells. Aliquots (5 μl each) of lysates expressing no protein (lane 1), ralGDS alone (lane 2), both ralGDS and v-ras p21 (lane 3), or both ralGDS and ras p21$^{S17N}$ (lane 4) were probed with the anti-ralGDS and ras p21 antibodies.
FIG. 2B shows the interaction of ralGDS with ras p21 in Sf9 cells. Sf9 cells expressing both ralGDS and v-ras p21 (lanes 1 and 3) and ralGDS alone (lane 2) were lysed, and the proteins of the lysates were immunoprecipitated (IP) with the anti-ras p21 antibody (Ab; lanes 1 and 2) or nonimmune rat immunoglobulin (Ig; lane 3). The precipitates were probed with the anti-ralGDS and ras p21 antibodies.
FIG. 2C shows the inability of ralGDS to interact with ras p21$^{S17N}$. Sf9 cells coexpressing ralGDS with v-ras p21 (lane 1) or ralGDS with ras p21$^{S17N}$ (lane 2) were lysed, and the proteins of the lysates were immunoprecipitated with the anti-ras p21 antibody. The precipitates were probed with the anti-ralGDS and ras p21 antibodies.
FIG. 2D shows the inability of Y13-259 to immunoprecipitate a ras p21-ralGDS complex. Sf9 cells expressing v-ras p21 alone (lanes 1 and 2) or both ralGDS and v-ras p21 (lanes 3 and 4) were lysed, and the proteins of the lysates were immunoprecipitated with Y13-238 (lanes 1 and 3) or Y13-259 (lanes 2 and 4). The precipitates were probed with the anti-ralGDS and ras p21 antibodies. An arrowhead and an arrow indicate the positions of ralGDS and ras p21, respectively. The results shown are representative of three independent experiments.

To examine whether ralGDS interacts with ras p21 in intact cells, ralGDS was coexpressed with v-ras p21 in insect cells. The expression level of transfected ralGDS in Sf9 cells expressing ralGDS alone was similar to that in the cells coexpressing ralGDS with v-ras p21, as assessed by immunoblotting (FIG. 2A, lanes 1 to 3). The lower band which is seen under ralGDS might be a degradation product of ralGDS. When the lysates coexpressing ralGDS with v-ras p21 were immunoprecipitated with the anti-ras p21 antibody, both ralGDS and ras p21 were detected in the ras p21 immune complex (FIG. 2B, lane 1). When the lysates expressing ralGDS alone or v-ras p21 alone were immunoprecipitated with the anti-ras p21 antibody, ralGDS was not detected (FIG. 2B, lane 2; FIG. 2D, lane 1). Neither ralGDS nor ras p21 was immunoprecipitated with nonimmune immunoglobulin in lysates expressing both proteins (FIG. 2B, lane 3).

TABLE 2

Interaction of ralGDS with ras p21 in the yeast two-hybrid system[a]

| GAL4 DNA-binding domain fusion | GAL4 transactivation domain fusion | β-Galactosidase activity |
|---|---|---|
| Vector | ralGDS | − |
| ras p21 | Vector | − |
| ras p21 | ralGDS | + |
| ras p21$^{C186S}$ | ralGDS | + |
| ras p21$^{T35A}$ | ralGDS | − |
| rap1 p21 | ralGDS | + |
| ralB p24 | ralGDS | − |
| rac1 p21$^{G12V}$ | ralGDS | − |

[a]Y153 was cotransformed with ralGDS and ras p21 mutants or other small G proteins and assayed for β-galactosidase activity. A blue signal, representing β-galactosidase activity, is indicated by a +, and a white signal, indicating a lack of β-galactosidase activity, is shown as a −. In each case, β-galactosidase expression was not detected when cells were transformed with the DNA-binding domain (amino acids 1 to 147) or the transactivation domain (amino acids 768 to 881) fusion alone.

To characterize the interaction of ralGDS and ras p21 further, the ability of ralGDS to interact with a ras p21 mutant, ras p21$^{S17N}$, was examined. ras p21$^{S17N}$ is well known as a dominant negative mutant that has higher affinity for GDP than GTP and strongly interacts with upstream molecules but not with downstream molecules (Barbacid, Annu. Rev. Biochem., 56:779–827 (1987); Farnsworth et al., Mol. Cell Biol., 11:4822–4829 (1991); Lowy et al., supra). The expression level of ras p21$^{S17N}$ was similar to that of V-ras p21 (FIG. 2A, lanes 3 and 4). When the lysates coexpressing ralGDS with ras p21$^{S17N}$ were immunoprecipitated with the antiras p21 antibody, ralGDS was not coprecipitated with ras p21$^{S17N}$ under the same conditions in which ralGDS was coprecipitated with v-ras p21 (FIG. 2C, lanes 1 and 2). These results indicate that ralGDS makes a complex with v-ras p21 but not with ras p21$^{S17N}$ in intact cells.

Y13-238 was used as the anti-ras p21 antibody to immunoprecipitate ras p21 for these experiments. Another antibody, Y13-259, was tested for its ability to immunoprecipitate a ras p21-ralGDS complex. Y13-259 is known to be a neutralizing antibody (Mulcahy et al., Nature (London), 313:241–243 (1995)). In contrast to Y13-238, Y13-259 could not immunoprecipitate the ras p21-ralGDS complex from the lysate coexpressing ralGDS with v-ras p21 under the same conditions (FIG. 2D, lanes 3 and 4). Y13-259 and Y13-238 immunoprecipitated similar amounts of ras p21 from the lysates expressing v-ras p21 alone (FIG. 2D, lanes 1 and 2).

Interaction of ralGDS with ras p21 in vitro.

Figures 3A, 3B:
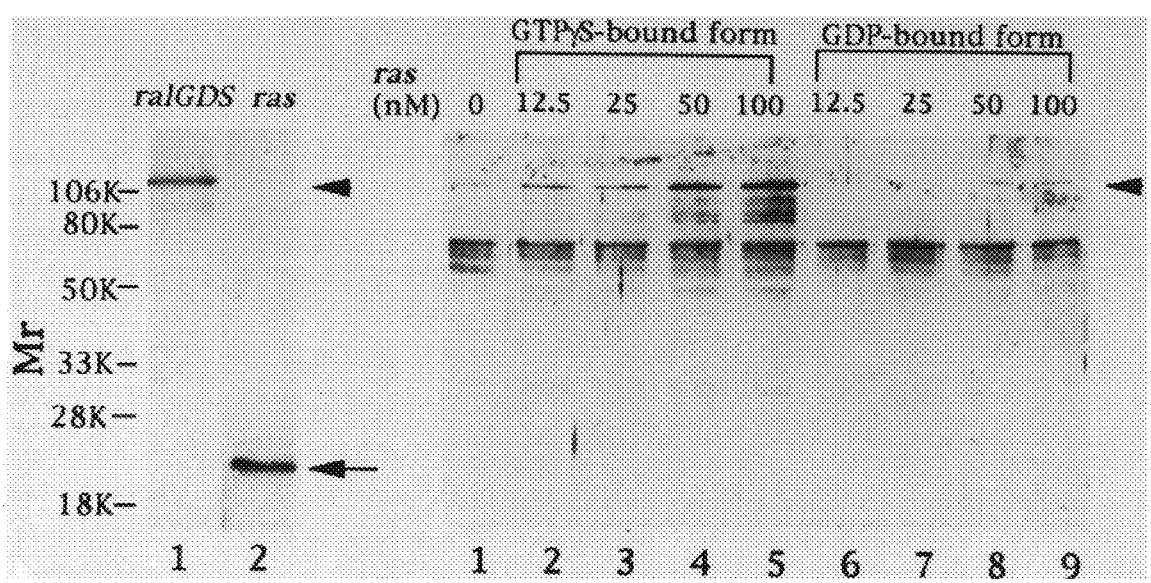
FIG. 3A shows the protein staining of ralGDS and c-ras p21. The purified ralGDS and c-ras p21 (0.5 μg of protein each) were subjected to SDS-PAGE (12% polyacrylamide gel) and stained with Coomassie brilliant blue.
FIG. 3B shows the interaction of ralGDS with the GTP-bound form of ras p21. ralGDS (20 pmol) was incubated without (lane 1) or with the indicated amounts of the GTPγS-bound form (lanes 2 to 5) or GDP-bound form (lanes 6 to 9) of ras p21, and the mixtures were immunoprecipitated with the anti-ras p21 antibody. The precipitates were probed with the anti-ralGDS antibody. An arrowhead and an arrow indicate the positions of ralGDS and ras p21, respectively. The results shown are representative of three independent experiments.
Figure 5:
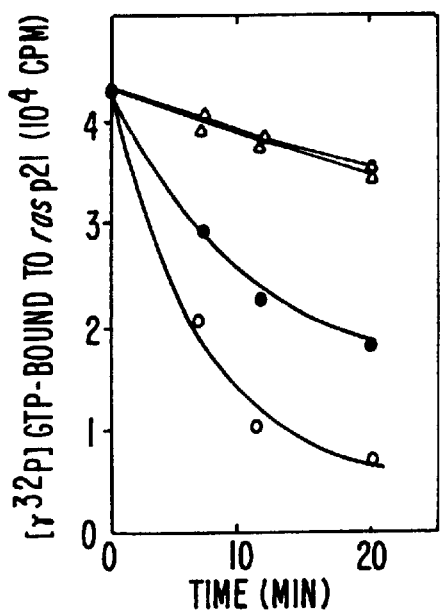
Figure 5:
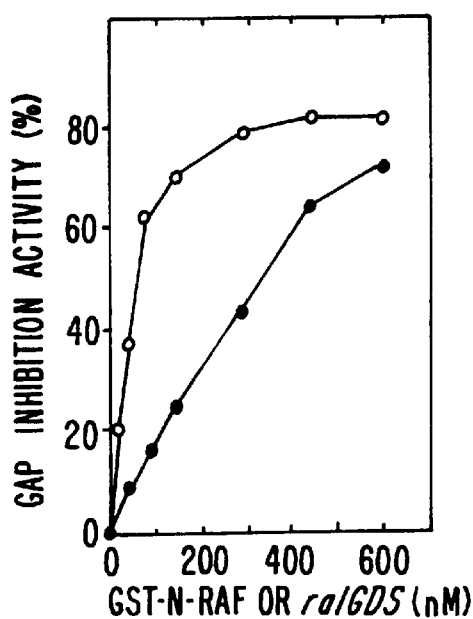
Figure 5:
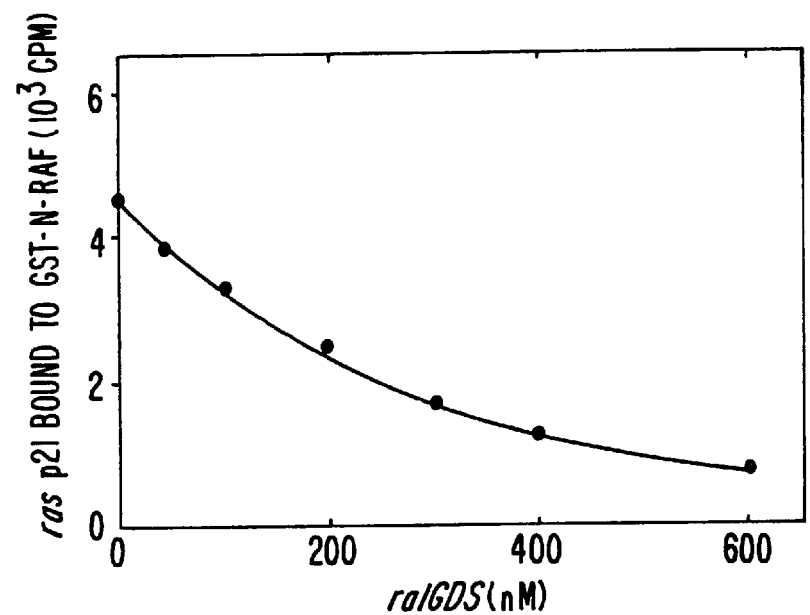

The interaction of ralGDS and ras p21 from the cytosolic fraction of insect cells was direct, ralGDS and ras p21 were purified from the cytosolic fraction of insect cells. The purity of both proteins was more than 95% by Coomassie brilliant blue staining (FIG. 3A). The GTPγS- or GDP-bound form of ras p21 was incubated with ralGDS, and this mixture was immunoprecipitated with the anti-ras p21 antibody. ralGDS was coprecipitated with the GTPγS-bound form of ras in a dose-dependent manner but not with the GDP-bound form (FIG. 3B).

Effect of ralGDS on the GAP Activity of NF1 for ras p21.

It has been reported that ralGDS does not affect the dissociation of GDP and GTP from ras p21 (Albright, supra). The effect of ralGDS on the GTPase activity of ras p21 was examined. ralGDS did not alter the intrinsic GTPase activity of ras p21 (FIG. 4A). In contrast, ralGDS inhibited the GAP activity of GST-NF1 for ras p21 at a 50% inhibitory dose (IC$_{50}$) of about 300 nM (FIG. 4). GST-N-Raf also inhibited the GAP activity of GST-NF1 at an IC$_{50}$ of about 50 nM under the same conditions (FIG. 4B). The IC$_{50}$ value of GST-N-Raf to inhibit the GAP activity of GST-NF1 was similar to previous observations (Warne et al., Nature (London), 364:352–355 (1993)). ralGDS did not interact with GST-NF1 (data not shown).

Effect of ralGDS on the interaction of Raf with ras p21.

Since Raf is an effector protein of ras p21, ralGDS was examined as to whether it inhibits the interaction of Raf with ras p21. GST-N-Raf interacted with ras p21 as described previously (Kikuchi et al., supra; Vojtek et al., Cell, 74:205–214 (1993); Warne, supra; Zhang et al., Nature (London), 364:308–313 (1993). ralGDS inhibited this interaction in a dose-dependent manner (FIG. 5). The IC$_{50}$ value of ralGDS to inhibit the interaction of Raf-1 with ras p21 was about 250 nM.

SUMMARY OF EXPERIMENTAL EXAMPLES

Using a yeast two-hybrid system, a novel protein which interacts with ras p21 was identified. This protein shares 69% amino acid homology with ral guanine nucleotide dissociation stimulator (ralGDS), a GDP/GTP exchange protein for ral p24. Hence, the designation of this novel protein as RGL, for ralGDS-like. It was found that an effector loop mutant of ras p21 was defective in interacting with the ras p21-interacting domain of RGL, indicating that this domain binds to ras p21 through the effector loop of ras p21. Since ralGDS contained a region highly homologous with the ras p21-interacting domain of RGL, ralGDS was examined for possible interaction with ras p21. ralGDS failed to interact with an effector loop mutant of ras p21. In insect cells, ralGDS made a complex with v-ras p21 but not with a dominant negative mutant of ras p21, ralGDS interacted with the GTP-bound form of ras p21 but not with the GDP-bound form in vitro. ralGDS inhibited both the GTPase-activating activity of the neurofibromatosis gene product (NF1) for ras p21 and the interaction of Raf with ras p21 in vitro. These results demonstrate that ralGDS specifically interacts with the active form of ras p21 and that ralGDS can compete with NF1 and Raf for binding to the effector loop of ras p21. Therefore, ralGDS family members likely are effector proteins of ras p21 or will inhibit interactions between ras p21 and its effectors.

All the information contained in the references and patent documents cited above is incorporated herein by reference.

What is claimed is:

1. A pharmaceutical composition comprising a RID polypeptide (SEQ. ID NO:4) and a pharmaceutically acceptable carrier.

2. An isolated polynucleotide comprising a nucleotide sequence encoding a protein comprising the amino acid sequence of SEQ. ID NO:2.

3. An isolated polynucleotide comprising a nucleotide sequence encoding a protein comprising the amino acid sequence of SEQ. ID NO:4.

4. A vector comprising the isolated polynucleotide of claim 2.

5. A vector comprising the isolated polynucleotide of claim 3.

6. A cell comprising the vector of claim 4.

7. A cell comprising the vector of claim 5.

8. An isolated DNA consisting of a fragment at least 40 nucleotides in length from the coding sequence of SEQ. ID NO:1.

9. An isolated nucleic acid encoding a polypeptide comprising at least 12 continuous amino acids from the amino acid sequence of SEQ. ID NO:4.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 2671 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 160..2463

(xi) SEQUENCE DESCRIPTION: SEQ ID NO:1:

```
AATTCGGCAC GAGGCGGTCG CGCGCGGCGG CGGCGGCGGC AGTCGGGCAG CAAGGCGCGT      60

GGGAAGCGCG GGGACCCGGA GCCGGGCCAG AGAGACGCCC CGACCGCCTC GGAGCAGGGC     120

GCACCATGCA GCGTCCGTGT GCCGGAAAGA AAACTGAGA ATG AAA TTA CTT TGG       174
                                           Met Lys Leu Leu Trp
                                             1               5

CAA GCT AAA ATG AGC TCG ATT CAG GAC TGG GGT GAA GAG GTA GAG GAA      222
Gln Ala Lys Met Ser Ser Ile Gln Asp Trp Gly Glu Glu Val Glu Glu
             10                  15                  20

GGA GCT GTT TAC CAT GTC ACC CTC AAA AGA GTC CAG ATT CAA CAG GCG      270
Gly Ala Val Tyr His Val Thr Leu Lys Arg Val Gln Ile Gln Gln Ala
         25                  30                  35

GCC AAT AAA GGA GCG AGA TGG CTA GGG GTT GAA GGG GAC CAG CTG CCT      318
Ala Asn Lys Gly Ala Arg Trp Leu Gly Val Glu Gly Asp Gln Leu Pro
     40                  45                  50

CCA GGA CAC ACA GTC AGT CAG TAC GAG ACC TGC AAG ATC AGG ACC ATC      366
Pro Gly His Thr Val Ser Gln Tyr Glu Thr Cys Lys Ile Arg Thr Ile
 55                  60                  65

AAA GCT GGT ACG CTG GAG AAG CTT GTG GAG AAC CTG CTG ACG GCT TTT      414
Lys Ala Gly Thr Leu Glu Lys Leu Val Glu Asn Leu Leu Thr Ala Phe
 70                  75                  80                  85

GGG GAC AAT GAC TTT ACC TAC ATC AGC ATC TTT TTG TCG ACA TAC AGA      462
Gly Asp Asn Asp Phe Thr Tyr Ile Ser Ile Phe Leu Ser Thr Tyr Arg
                 90                  95                 100

GGC TTT GCC TCG ACT AAG GAA GTG CTG GAG CTG CTG GAC AGG TAT          510
Gly Phe Ala Ser Thr Lys Glu Val Leu Glu Leu Leu Asp Arg Tyr
             105                 110                 115

GGA AAC CTG ACA GGC CCA AAC TGT GAA GAC GAT GGA AGC CAA AGT TCA      558
Gly Asn Leu Thr Gly Pro Asn Cys Glu Asp Asp Gly Ser Gln Ser Ser
             120                 125                 130

CCC GAG TCC AAG GCC GTG ATC CGG AAT GCC ATT GCT TCC ATC CTG AGG      606
Pro Glu Ser Lys Ala Val Ile Arg Asn Ala Ile Ala Ser Ile Leu Arg
 135                 140                 145

GCC TGG CTT GAC CAG TGT GCG GAA GAC TTC CGG GAG CCC CCT CAC TTC      654
Ala Trp Leu Asp Gln Cys Ala Glu Asp Phe Arg Glu Pro Pro His Phe
 150                 155                 160                 165

CCT TGC CTT CAG AAG CTG CTG GAG TAC CTC AAA CAG ATG ATG CCT GGC      702
Pro Cys Leu Gln Lys Leu Leu Glu Tyr Leu Lys Gln Met Met Pro Gly
                 170                 175                 180

TCT GAC CCA GAG AGG AGA GCA CAG AAC CTT CTT GAA CAG TTT CAA AAG      750
Ser Asp Pro Glu Arg Arg Ala Gln Asn Leu Leu Glu Gln Phe Gln Lys
             185                 190                 195
```

```
CAG GAC GTG GAT TCC GAC AAT GGA CTT CTC AAC ACC AGC TCC TTC AGC        798
Gln Asp Val Asp Ser Asp Asn Gly Leu Leu Asn Thr Ser Ser Phe Ser
            200                 205                 210

CTG GAA GAG GAA GAG GAA CTG GAG AGC GGA GGG TCA GCA GAA TTC ACG        846
Leu Glu Glu Glu Glu Glu Leu Glu Ser Gly Gly Ser Ala Glu Phe Thr
    215                 220                 225

AAC TTC TCA GAA GAT CTC GTG GCA GAA CAG CTG ACC TAC ATG GAC GCA        894
Asn Phe Ser Glu Asp Leu Val Ala Glu Gln Leu Thr Tyr Met Asp Ala
230                 235                 240                 245

CAA CTA TTC AAG AAG GTA GTG CCT CAC CAT TGC CTG GGC TGT ATT TGG        942
Gln Leu Phe Lys Lys Val Val Pro His His Cys Leu Gly Cys Ile Trp
            250                 255                 260

TCT CAG CGG GAT AAA AAG GAA AAC AAG CAT TTG GCT CCT ACG ATC CGT        990
Ser Gln Arg Asp Lys Lys Glu Asn Lys His Leu Ala Pro Thr Ile Arg
        265                 270                 275

GCC ACC ATC TCT CAG TTT AAT ACG CTC ACC AAG TGT GTT GTC AGC ACC       1038
Ala Thr Ile Ser Gln Phe Asn Thr Leu Thr Lys Cys Val Val Ser Thr
    280                 285                 290

GTC CTG GGG AGC AAG GAA CTC AAA ACT CAG CAG CGA GCC AGA GTC ATC       1086
Val Leu Gly Ser Lys Glu Leu Lys Thr Gln Gln Arg Ala Arg Val Ile
295                 300                 305

GAG AAG TGG ATC AAC ATT GCT CAC GAA TGT AGA ATC CTG AAG AAT TTT       1134
Glu Lys Trp Ile Asn Ile Ala His Glu Cys Arg Ile Leu Lys Asn Phe
310                 315                 320                 325

TCC TCC TTG AGG GCC ATC GTT TCC GCA CTG CAG TCT AAT TCC ATC TAT       1182
Ser Ser Leu Arg Ala Ile Val Ser Ala Leu Gln Ser Asn Ser Ile Tyr
            330                 335                 340

CGG TTG AAA AAG GCT TGG GCT GCT GTC CCG AAG GAC AGA ATG CTG ATG       1230
Arg Leu Lys Lys Ala Trp Ala Ala Val Pro Lys Asp Arg Met Leu Met
        345                 350                 355

TTT GAA GAA CTT TCA GAT ATC TTC TCT GAT CAC AAT AAC CAT CTA ACC       1278
Phe Glu Glu Leu Ser Asp Ile Phe Ser Asp His Asn Asn His Leu Thr
    360                 365                 370

AGT CGG GAG CTA CTA ATG AAG GAA GGA ACT TCA AAA TTT GCA AAC CTG       1326
Ser Arg Glu Leu Leu Met Lys Glu Gly Thr Ser Lys Phe Ala Asn Leu
375                 380                 385

GAC AGC AGC GTG AAA GAA AAC CAG AAG CGG ACC CAG AGG CGC CTG CAA       1374
Asp Ser Ser Val Lys Glu Asn Gln Lys Arg Thr Gln Arg Arg Leu Gln
390                 395                 400                 405

CTG CAG AAG GAT ATG GGT GTG ATG CAG GGT ACC GTG CCT TAC CTG GGC       1422
Leu Gln Lys Asp Met Gly Val Met Gln Gly Thr Val Pro Tyr Leu Gly
            410                 415                 420

ACC TTC CTG ACT GAC CTG ACC ATG CTG GAC ACT GCC CTG CAG GAC TAC       1470
Thr Phe Leu Thr Asp Leu Thr Met Leu Asp Thr Ala Leu Gln Asp Tyr
        425                 430                 435

ATT GAG GGT GGA CTG ATC AAC TTC GAG AAA AGA AGA AGG GAA TTT GAA       1518
Ile Glu Gly Gly Leu Ile Asn Phe Glu Lys Arg Arg Arg Glu Phe Glu
    440                 445                 450

GTC ATT GCC CAG ATA AAG CTC CTA CAG TCT GCT TGC AAC AGC TAC TGC       1566
Val Ile Ala Gln Ile Lys Leu Leu Gln Ser Ala Cys Asn Ser Tyr Cys
455                 460                 465

ATG GGC CCA GAC CAG AAG TTT ATC CAG TGG TTC CAG AGG CAG CAG CTT       1614
Met Gly Pro Asp Gln Lys Phe Ile Gln Trp Phe Gln Arg Gln Gln Leu
470                 475                 480                 485

CTA TCA GAG GAG GAA AGC TAC GCC CTC TCG TGT GAG ATT GAA GCC GCT       1662
Leu Ser Glu Glu Glu Ser Tyr Ala Leu Ser Cys Glu Ile Glu Ala Ala
            490                 495                 500

GCC GAC GCC AAC ACC ACT TCC CCT AAG CCT CGG AAA AGC ATG GTG AAG       1710
Ala Asp Ala Asn Thr Thr Ser Pro Lys Pro Arg Lys Ser Met Val Lys
        505                 510                 515
```

| | | | | | | | | | | | | | | |
|---|---|---|---|---|---|---|---|---|---|---|---|---|---|---|
| AGG | CTG | AGC | CTG | CTA | TTT | CTG | GGG | TCT | GAC | ATC | ATC | CCC | GGG | AGC | ACT | 1758
| Arg | Leu | Ser | Leu | Leu | Phe | Leu | Gly | Ser | Asp | Ile | Ile | Pro | Gly | Ser | Thr |
| | 520 | | | | | 525 | | | | | 530 | | | | |

```
AGG CTG AGC CTG CTA TTT CTG GGG TCT GAC ATC ATC CCC GGG AGC ACT           1758
Arg Leu Ser Leu Leu Phe Leu Gly Ser Asp Ile Ile Pro Gly Ser Thr
        520                 525                 530

CCC ACC AAA GAG CAG CCC AAG TCC GCA GCC AGT GGG AGC TCT GGG GAG           1806
Pro Thr Lys Glu Gln Pro Lys Ser Ala Ala Ser Gly Ser Ser Gly Glu
        535                 540                 545

AGT ATG GAC TCA GTC AGT GTG TCG TCC TGT GAA TCA AAC CAC TCC GAG           1854
Ser Met Asp Ser Val Ser Val Ser Ser Cys Glu Ser Asn His Ser Glu
550                 555                 560                 565

GCT GAG GAG GGC CCC GTC ACA CCC ATG GAC ACA CCA GAT GAG CCC CAA           1902
Ala Glu Glu Gly Pro Val Thr Pro Met Asp Thr Pro Asp Glu Pro Gln
        570                 575                 580

AAG AAG CTC TCT GAA TCC TCC TCT TCC TGT TCC TCC ATC CAT TCC ATG           1950
Lys Lys Leu Ser Glu Ser Ser Ser Ser Cys Ser Ser Ile His Ser Met
        585                 590                 595

GAC ACG AAT TCC TCA GGG ATG TCG TCC CTA ATC AAC CCC CTG TCC TCC           1998
Asp Thr Asn Ser Ser Gly Met Ser Ser Leu Ile Asn Pro Leu Ser Ser
        600                 605                 610

CCT CCA ACG TGC AAC AAC AAT CCT AAA ATC CAC AAG CGC TCC GTC TCC           2046
Pro Pro Thr Cys Asn Asn Asn Pro Lys Ile His Lys Arg Ser Val Ser
        615                 620                 625

GTG ACA TCC ATT ACC TCC ACA GTA CTG CCT CCT GTT TAC AAT CAG CAG           2094
Val Thr Ser Ile Thr Ser Thr Val Leu Pro Pro Val Tyr Asn Gln Gln
630                 635                 640                 645

AAC GAA GAC ACC TGC ATC ATC CGC ATC AGT GTA GAA GAC AAC AAT GGC           2142
Asn Glu Asp Thr Cys Ile Ile Arg Ile Ser Val Glu Asp Asn Asn Gly
                650                 655                 660

CAC ATG TAC AAG AGC ATC ATG CTG ACA AGC CAG GAT AAG ACC CCC GCT           2190
His Met Tyr Lys Ser Ile Met Leu Thr Ser Gln Asp Lys Thr Pro Ala
        665                 670                 675

GTG ATC CAG AGA GCG ATG TCG AAG CAC AAC CTG GAG TCG GAC CCC GCC           2238
Val Ile Gln Arg Ala Met Ser Lys His Asn Leu Glu Ser Asp Pro Ala
        680                 685                 690

GAG GAG TAT GAG CTG GTG CAG GTC ATC TCG GAG GAC AAA GAA CTA GTG           2286
Glu Glu Tyr Glu Leu Val Gln Val Ile Ser Glu Asp Lys Glu Leu Val
        695                 700                 705

ATC CCG GAC TCT GCA AAC GTC TTT TAC GCC ATG AAT AGC CAA GTG AAC           2334
Ile Pro Asp Ser Ala Asn Val Phe Tyr Ala Met Asn Ser Gln Val Asn
710                 715                 720                 725

TTT GAT TTC ATT TTA CGC AAA AAG AAC TCG GTG GAG GAG CAG GTG AAG           2382
Phe Asp Phe Ile Leu Arg Lys Lys Asn Ser Val Glu Glu Gln Val Lys
                730                 735                 740

TTG CGC AGT CGG ACC AGC CTG ACT TTG CCC AGG ACA GCT AAG CGG GGC           2430
Leu Arg Ser Arg Thr Ser Leu Thr Leu Pro Arg Thr Ala Lys Arg Gly
        745                 750                 755

TGC TGG AGT AAC AGG CAC AGC AAG ATC ACC CTC T GAAAGGGACA                  2474
Cys Trp Ser Asn Arg His Ser Lys Ile Thr Leu
760                 765

GTACACTCCT ACTGCCCAAG GCAGAGTGAG GCTGAGCAAA AGCCATGGCG ACGCCAACCA         2534

CCACCCAGTG TTGAGCATCA TTGGTGAAAG CGACAGATAT TTATAGAATT CAGCTGTGCA         2594

GAGAGCACTG TGCAGGGGAG AGTGGAAGTG AATTTGACAT TAAAAGGATA AAAGGTTCAA         2654

AAAAAAAAAA AAAAAAA                                                       2671

(2) INFORMATION FOR SEQ ID NO:2:

(i) SEQUENCE CHARACTERISTICS:
        (A) LENGTH: 768 amino acids
        (B) TYPE: amino acid
        (D) TOPOLOGY: linear
```

(ii) MOLECULE TYPE: protein (xi) SEQUENCE DESCRIPTION: SEQ ID NO:2:

```
Met Lys Leu Leu Trp Gln Ala Lys Met Ser Ser Ile Gln Asp Trp Gly
 1               5                  10                  15

Glu Glu Val Glu Glu Gly Ala Val Tyr His Val Thr Leu Lys Arg Val
                20                  25                  30

Gln Ile Gln Gln Ala Ala Asn Lys Gly Ala Arg Trp Leu Gly Val Glu
            35                  40                  45

Gly Asp Gln Leu Pro Pro Gly His Thr Val Ser Gln Tyr Glu Thr Cys
    50                  55                  60

Lys Ile Arg Thr Ile Lys Ala Gly Thr Leu Glu Lys Leu Val Glu Asn
65                  70                  75                  80

Leu Leu Thr Ala Phe Gly Asp Asn Asp Phe Thr Tyr Ile Ser Ile Phe
                85                  90                  95

Leu Ser Thr Tyr Arg Gly Phe Ala Ser Thr Lys Glu Val Leu Glu Leu
            100                 105                 110

Leu Leu Asp Arg Tyr Gly Asn Leu Thr Gly Pro Asn Cys Glu Asp Asp
        115                 120                 125

Gly Ser Gln Ser Ser Pro Glu Ser Lys Ala Val Ile Arg Asn Ala Ile
    130                 135                 140

Ala Ser Ile Leu Arg Ala Trp Leu Asp Gln Cys Ala Glu Asp Phe Arg
145                 150                 155                 160

Glu Pro Pro His Phe Pro Cys Leu Gln Lys Leu Leu Glu Tyr Leu Lys
                165                 170                 175

Gln Met Met Pro Gly Ser Asp Pro Glu Arg Arg Ala Gln Asn Leu Leu
            180                 185                 190

Glu Gln Phe Gln Lys Gln Asp Val Asp Ser Asp Asn Gly Leu Leu Asn
        195                 200                 205

Thr Ser Ser Phe Ser Leu Glu Glu Glu Glu Leu Glu Ser Gly Gly
    210                 215                 220

Ser Ala Glu Phe Thr Asn Phe Ser Glu Asp Leu Val Ala Glu Gln Leu
225                 230                 235                 240

Thr Tyr Met Asp Ala Gln Leu Phe Lys Lys Val Val Pro His His Cys
                245                 250                 255

Leu Gly Cys Ile Trp Ser Gln Arg Asp Lys Lys Glu Asn Lys His Leu
            260                 265                 270

Ala Pro Thr Ile Arg Ala Thr Ile Ser Gln Phe Asn Thr Leu Thr Lys
        275                 280                 285

Cys Val Val Ser Thr Val Leu Gly Ser Lys Glu Leu Lys Thr Gln Gln
    290                 295                 300

Arg Ala Arg Val Ile Glu Lys Trp Ile Asn Ile Ala His Glu Cys Arg
305                 310                 315                 320

Ile Leu Lys Asn Phe Ser Ser Leu Arg Ala Ile Val Ser Ala Leu Gln
                325                 330                 335

Ser Asn Ser Ile Tyr Arg Leu Lys Lys Ala Trp Ala Ala Val Pro Lys
            340                 345                 350

Asp Arg Met Leu Met Phe Glu Glu Leu Ser Asp Ile Phe Ser Asp His
        355                 360                 365

Asn Asn His Leu Thr Ser Arg Glu Leu Leu Met Lys Glu Gly Thr Ser
    370                 375                 380

Lys Phe Ala Asn Leu Asp Ser Ser Val Lys Glu Asn Gln Lys Arg Thr
385                 390                 395                 400

Gln Arg Arg Leu Gln Leu Gln Lys Asp Met Gly Val Met Gln Gly Thr
```

```
                    405                 410                 415
Val Pro Tyr Leu Gly Thr Phe Leu Thr Asp Leu Thr Met Leu Asp Thr
                420                 425                 430

Ala Leu Gln Asp Tyr Ile Glu Gly Gly Leu Ile Asn Phe Glu Lys Arg
            435                 440                 445

Arg Arg Glu Phe Glu Val Ile Ala Gln Ile Lys Leu Leu Gln Ser Ala
        450                 455                 460

Cys Asn Ser Tyr Cys Met Gly Pro Asp Gln Lys Phe Ile Gln Trp Phe
465                 470                 475                 480

Gln Arg Gln Gln Leu Leu Ser Glu Glu Ser Tyr Ala Leu Ser Cys
                485                 490                 495

Glu Ile Glu Ala Ala Ala Asp Ala Asn Thr Thr Ser Pro Lys Pro Arg
                500                 505                 510

Lys Ser Met Val Lys Arg Leu Ser Leu Leu Phe Leu Gly Ser Asp Ile
            515                 520                 525

Ile Pro Gly Ser Thr Pro Thr Lys Glu Gln Pro Lys Ser Ala Ala Ser
        530                 535                 540

Gly Ser Ser Gly Glu Ser Met Asp Ser Val Ser Ser Cys Glu
545                 550                 555                 560

Ser Asn His Ser Glu Ala Glu Glu Gly Pro Val Thr Pro Met Asp Thr
                565                 570                 575

Pro Asp Glu Pro Gln Lys Lys Leu Ser Glu Ser Ser Ser Cys Ser
            580                 585                 590

Ser Ile His Ser Met Asp Thr Asn Ser Ser Gly Met Ser Ser Leu Ile
        595                 600                 605

Asn Pro Leu Ser Ser Pro Pro Thr Cys Asn Asn Pro Lys Ile His
610                 615                 620

Lys Arg Ser Val Ser Val Thr Ser Ile Thr Ser Thr Val Leu Pro Pro
625                 630                 635                 640

Val Tyr Asn Gln Gln Asn Glu Asp Thr Cys Ile Ile Arg Ile Ser Val
                645                 650                 655

Glu Asp Asn Asn Gly His Met Tyr Lys Ser Ile Met Leu Thr Ser Gln
            660                 665                 670

Asp Lys Thr Pro Ala Val Ile Gln Arg Ala Met Ser Lys His Asn Leu
        675                 680                 685

Glu Ser Asp Pro Ala Glu Glu Tyr Glu Leu Val Gln Val Ile Ser Glu
690                 695                 700

Asp Lys Glu Leu Val Ile Pro Asp Ser Ala Asn Val Phe Tyr Ala Met
705                 710                 715                 720

Asn Ser Gln Val Asn Phe Asp Phe Ile Leu Arg Lys Lys Asn Ser Val
                725                 730                 735

Glu Glu Gln Val Lys Leu Arg Ser Arg Thr Ser Leu Thr Leu Pro Arg
            740                 745                 750

Thr Ala Lys Arg Gly Cys Trp Ser Asn Arg His Ser Lys Ile Thr Leu
        755                 760                 765

(2) INFORMATION FOR SEQ ID NO:3:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:
```

```
TCGTCCCTAA TCAACCCCCT GTCCTCCCCT CCAACGTGCA CAACAATCC  TAAAATCCAC         60

AAGCGCTCCG TCTCCGTGAC ATCCATTACC TCCACAGTAC TGCCTCCTGT TTACAATCAG        120

CAGAACGAAG ACACCTGCAT CATCCGCATC AGTGTAGAAG ACAACAATGG CCACATGTAC        180

AAGAGCATCA TGCTGACAAG CCAGGATAAG ACCCCCGCTG TGATCCAGAG AGCGATGTCG        240

AAGCACAACC TGGAGTCGGA CCCCGCCGAG GAGTATGAGC TGGTGCAGGT CATCTCGGAG        300

GACAAAGAAC TAGTGATCCC GGACTCTGCA AACGTCTTTT ACGCCATGAA TAGCCAAGTG        360

AACTTTGATT TCATTTTACG CAAAAAGAAC TCGGTGGAGG AGCAGGTGAA GTTGCGCAGT        420

CGGACCAGCC TGACTTTGCC CAGGACAGCT AAGCGGGGCT GCTGGAGTAA CAGGCACAGC        480

AAGATCACCC TC                                                            492
```

(2) INFORMATION FOR SEQ ID NO:4:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Ser Ser Leu Ile Asn Pro Leu Ser Ser Pro Thr Cys Asn Asn Asn
1               5                   10                  15

Pro Lys Ile His Lys Arg Ser Val Ser Val Thr Ser Ile Thr Ser Thr
            20                  25                  30

Val Leu Pro Pro Val Tyr Asn Gln Gln Asn Glu Asp Thr Cys Ile Ile
            35                  40                  45

Arg Ile Ser Val Glu Asp Asn Asn Gly His Met Tyr Lys Ser Ile Met
        50                  55                  60

Leu Thr Ser Gln Asp Lys Thr Pro Ala Val Ile Gln Arg Ala Met Ser
65                  70                  75                  80

Lys His Asn Leu Glu Ser Asp Pro Ala Glu Glu Tyr Glu Leu Val Gln
                85                  90                  95

Val Ile Ser Glu Asp Lys Glu Leu Val Ile Pro Asp Ser Ala Asn Val
            100                 105                 110

Phe Tyr Ala Met Asn Ser Gln Val Asn Phe Asp Phe Ile Leu Arg Lys
            115                 120                 125

Lys Asn Ser Val Glu Glu Gln Val Lys Leu Arg Ser Arg Thr Ser Leu
        130                 135                 140

Thr Leu Pro Arg Thr Ala Lys Arg Gly Cys Trp Ser Asn Arg His Ser
145                 150                 155                 160

Lys Ile Thr Leu
```

(2) INFORMATION FOR SEQ ID NO:5:

(i) SEQUENCE CHARACTERISTICS:
        (A) LENGTH: 852 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Met Val Asp Cys Gln Ser Ser Thr Gln Glu Ile Gly Glu Glu Leu
1               5                   10                  15
```

```
Ile Asn Gly Val Ile Tyr Ser Ile Ser Leu Arg Lys Val Gln Leu His
             20                  25                  30

Gln Gly Ala Thr Lys Gly Gln Arg Trp Leu Gly Cys Glu Asn Glu Ser
             35                  40                  45

Ala Leu Asn Leu Tyr Glu Thr Cys Lys Val Arg Thr Val Lys Ala Gly
 50                  55                  60

Thr Leu Glu Lys Leu Val Glu His Leu Val Pro Ala Phe Gln Gly Ser
 65                  70                  75                  80

Asp Leu Ser Tyr Val Thr Val Phe Leu Cys Thr Tyr Arg Ala Phe Thr
                 85                  90                  95

Thr Thr Gln Gln Val Leu Asp Leu Leu Phe Lys Arg Tyr Gly Arg Cys
                100                 105                 110

Asp Ala Leu Thr Ala Ser Ser Arg Tyr Gly Cys Ile Leu Pro Tyr Ser
                115                 120                 125

Ser Glu Asp Gly Gly Pro Gln Asp Gln Leu Lys Asn Ala Ile Ser Ser
130                 135                 140

Ile Leu Gly Thr Trp Leu Asp Gln Tyr Ser Glu Asp Phe Cys Gln Pro
145                 150                 155                 160

Pro Asp Phe Pro Cys Leu Lys Gln Leu Val Ala Tyr Val Gln Leu Asn
                165                 170                 175

Met Pro Gly Ser Asp Leu Glu Arg Arg Ala His Leu Leu Leu Ala Gln
                180                 185                 190

Leu Glu Asp Leu Glu Pro Ser Glu Ala Glu Ser Glu Ala Leu Ser Pro
            195                 200                 205

Ala Pro Val Leu Ser Leu Lys Pro Ala Ser Gln Leu Glu Pro Ala Leu
210                 215                 220

Leu Leu Thr Pro Ser Gln Val Val Thr Ser Thr Pro Val Arg Glu Pro
225                 230                 235                 240

Ala Ala Ala Pro Val Pro Val Leu Ala Ser Ser Pro Val Val Ala Pro
                245                 250                 255

Ala Pro Glu Leu Glu Pro Val Pro Glu Pro Gln Glu Pro Glu Pro
                260                 265                 270

Ser Leu Ala Leu Ala Pro Glu Leu Glu Pro Ala Val Ser Gln Ser Leu
            275                 280                 285

Glu Leu Glu Ser Ala Pro Val Pro Thr Pro Ala Leu Glu Pro Ser Trp
290                 295                 300

Ser Leu Pro Glu Ala Thr Glu Asn Gly Leu Thr Glu Lys Pro His Leu
305                 310                 315                 320

Leu Leu Phe Pro Pro Asp Leu Val Ala Glu Gln Phe Thr Leu Met Asp
                325                 330                 335

Ala Glu Leu Phe Lys Lys Val Val Pro Tyr His Cys Leu Gly Ser Ile
                340                 345                 350

Trp Ser Gln Arg Ala Lys Lys Gly Lys Glu His Leu Ala Pro Thr Ile
            355                 360                 365

Arg Ala Thr Val Ala Gln Phe Asn Asn Val Ala Asn Cys Val Ile Thr
370                 375                 380

Thr Cys Leu Gly Asp Gln Ser Met Lys Ala Pro Asp Arg Ala Arg Val
385                 390                 395                 400

Val Glu His Trp Ile Glu Val Ala Arg Glu Cys Arg Ala Leu Lys Asn
                405                 410                 415

Phe Ser Ser Leu Tyr Ala Ile Leu Ser Ala Leu Gln Ser Asn Ala Ile
                420                 425                 430

His Arg Leu Lys Lys Thr Trp Glu Glu Val Ser Arg Asp Ser Phe Arg
            435                 440                 445
```

```
Val Phe Gln Lys Leu Ser Glu Ile Phe Ser Asp Glu Asn Asn Tyr Ser
    450                 455                 460

Leu Ser Arg Glu Leu Leu Ile Lys Glu Gly Thr Ser Lys Phe Ala Thr
465                 470                 475                 480

Ile Glu Met Asn Pro Arg Arg Ala Gln Arg Gln Lys Glu Thr Gly
                485                 490                 495

Val Ile Gln Gly Thr Val Pro Tyr Leu Gly Thr Phe Leu Thr Asp Leu
            500                 505                 510

Val Met Leu Asp Thr Ala Met Lys Asp Tyr Leu Tyr Gly Arg Leu Ile
    515                 520                 525

Asn Phe Glu Lys Arg Arg Lys Glu Phe Glu Val Ile Ala Gln Ile Lys
    530                 535                 540

Leu Leu Gln Ser Ala Cys Asn Asn Tyr Ser Ile Ala Pro Glu Glu His
545                 550                 555                 560

Phe Gly Thr Trp Phe Arg Ala Met Glu Arg Leu Ser Glu Ala Glu Ser
                565                 570                 575

Tyr Thr Leu Ser Cys Glu Leu Glu Pro Pro Ser Glu Ser Ala Ser Asn
            580                 585                 590

Thr Leu Arg Ser Lys Lys Ser Thr Ala Ile Val Lys Arg Trp Ser Asp
        595                 600                 605

Arg Gln Ala Pro Ser Thr Glu Leu Ser Thr Ser Ser Ser Ala His Ser
    610                 615                 620

Lys Ser Cys Asp Gln Leu Arg Cys Ser Pro Tyr Leu Gly Ser Gly Asp
625                 630                 635                 640

Ile Thr Asp Ala Leu Ser Val His Ser Ala Gly Ser Ser Ser Ser Asp
                645                 650                 655

Val Glu Glu Ile Asn Met Ser Phe Val Pro Glu Ser Pro Asp Gly Gln
            660                 665                 670

Glu Lys Lys Phe Trp Glu Ser Ala Ser Gln Ser Ser Pro Glu Thr Ser
        675                 680                 685

Gly Ile Thr Ser Ala Ser Ser Ser Thr Ser Ser Ser Ser Ala Ser Thr
    690                 695                 700

Thr Pro Val Ser Thr Thr Arg Thr His Lys Arg Ser Val Ser Gly Val
705                 710                 715                 720

Cys Ser Tyr Ser Ser Leu Pro Leu Tyr Asn Gln Gln Val Gly Asp
                725                 730                 735

Cys Cys Ile Ile Arg Val Ser Leu Asp Val Asp Asn Gly Asn Met Tyr
                740                 745                 750

Lys Ser Ile Leu Val Thr Ser Gln Asp Lys Ala Pro Thr Val Ile Arg
            755                 760                 765

Lys Ala Met Asp Lys His Asn Leu Asp Glu Asp Glu Pro Glu Asp Tyr
    770                 775                 780

Glu Leu Val Gln Ile Ile Ser Glu Asp His Lys Leu Lys Ile Pro Glu
785                 790                 795                 800

Asn Ala Asn Val Phe Tyr Ala Met Asn Ser Thr Ala Asn Tyr Asp Phe
                805                 810                 815

Ile Leu Lys Lys Arg Thr Phe Thr Lys Gly Ala Lys Val Lys His Gly
            820                 825                 830

Ala Ser Ser Thr Leu Pro Arg Met Lys Gln Lys Gly Leu Arg Ile Ala
    835                 840                 845

Lys Gly Ile Phe
850
```